(12) United States Patent
Noda et al.

(10) Patent No.: US 8,585,673 B2
(45) Date of Patent: Nov. 19, 2013

(54) ABSORBENT ARTICLE

(75) Inventors: Yuki Noda, Kagawa (JP); Kenichiro Kuroda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 614 days.

(21) Appl. No.: 12/302,397

(22) PCT Filed: Jun. 1, 2007

(86) PCT No.: PCT/JP2007/061205
§ 371 (c)(1),
(2), (4) Date: Nov. 25, 2008

(87) PCT Pub. No.: WO2007/142146
PCT Pub. Date: Dec. 13, 2007

(65) Prior Publication Data
US 2009/0281515 A1    Nov. 12, 2009

(30) Foreign Application Priority Data
Jun. 2, 2006  (JP) .................. 2006-155115

(51) Int. Cl.
A61F 13/20    (2006.01)
(52) U.S. Cl.
USPC ........................................... 604/392
(58) Field of Classification Search
USPC ......... 604/392, 393, 386, 389, 391, 397, 398, 604/400, 401
See application file for complete search history.

(56) References Cited

U.S. PATENT DOCUMENTS 5,611,790 A * 3/1997 Osborn et al. ................ 604/391
5,722,967 A   3/1998 Coles
(Continued)

FOREIGN PATENT DOCUMENTS

| JP | H03-101933 U | 10/1991 |
|----|--------------|---------|
| JP | H11-099179 A | 4/1999 |

(Continued)

OTHER PUBLICATIONS

European Search Report issued to EP Patent Application No. 07744592.2 mailed Jul. 8, 2011.

*Primary Examiner* — Lynne Anderson
*Assistant Examiner* — Bradley Philips
(74) *Attorney, Agent, or Firm* — Lowe Hauptman & Ham, LLP

(57) ABSTRACT

An absorbent article that can attain altering of the sensation of fitness thereof while maintaining a given capability of leakage prevention. The absorbent article is one comprising an absorbent article main body including at least a surface sheet part whose at least one area is permeable for liquid, disposed on one side in the direction of the thickness of the absorbent article and a liquid-retaining absorbent part disposed on the surface sheet part on the other side in the above direction of the thickness, and comprising, disposed on the other side in the direction of the thickness of the absorbent article main body, belt member (10) arranged so as to extend along the longitudinal direction (LD) of the absorbent article main body, the absorbent article shaped substantially longitudinally long. The belt member (10) has such a deformation region that at least portion thereof can be deformed so as to narrow in its width direction (WD). Further, the belt member (10) on its side of at least one end thereof in the longitudinal direction (LD) is provided with locking part (9f, 9r). The absorbent article main body and the belt member (10) in the deformation region are joined together at junction portions (8L, 8R) set apart from each other with a given spacing so as to have the center of the absorbent article main body in its width direction (WD) interposed therebetween.

7 Claims, 37 Drawing Sheets

(56) References Cited

U.S. PATENT DOCUMENTS

| | | | |
|---|---|---|---|
| 5,827,261 A * | 10/1998 | Osborn et al. | 604/387 |
| 6,221,062 B1 * | 4/2001 | Osborn, III | 604/385.23 |
| 6,413,249 B1 * | 7/2002 | Turi et al. | 604/387 |
| 7,125,401 B2 * | 10/2006 | Yoshimasa | 604/392 |
| 7,240,375 B2 * | 7/2007 | Martz | 2/406 |
| 7,908,824 B2 * | 3/2011 | Kuroda et al. | 53/416 |
| 2004/0147894 A1 * | 7/2004 | Mizutani et al. | 604/385.17 |
| 2007/0282287 A1 * | 12/2007 | Noda et al. | 604/385.16 |
| 2009/0240225 A1 * | 9/2009 | Noda et al. | 604/378 |
| 2009/0281515 A1 * | 11/2009 | Noda et al. | 604/392 |
| 2010/0010463 A1 * | 1/2010 | Kudo et al. | 604/378 |
| 2010/0274210 A1 * | 10/2010 | Noda et al. | 604/385.05 |
| 2010/0305541 A1 * | 12/2010 | Noda et al. | 604/385.04 |

FOREIGN PATENT DOCUMENTS

| | | |
|---|---|---|
| JP | 2005-095510 A | 4/2005 |
| JP | 2007-319543 A | 12/2007 |
| JP | 2007-319544 A | 12/2007 |
| JP | 2008-006270 A | 1/2008 |
| JP | 2008-023248 A | 2/2008 |

* cited by examiner

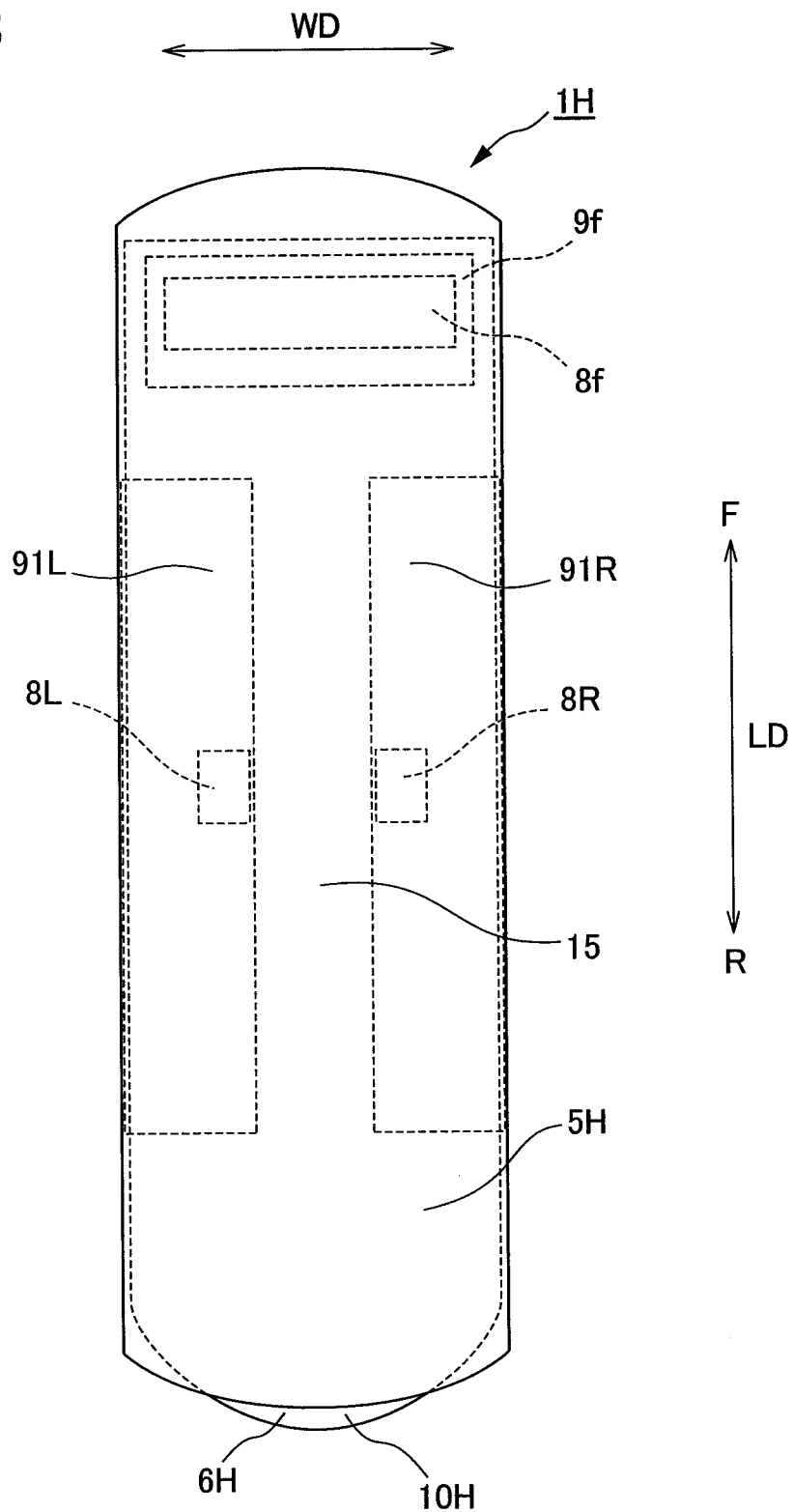

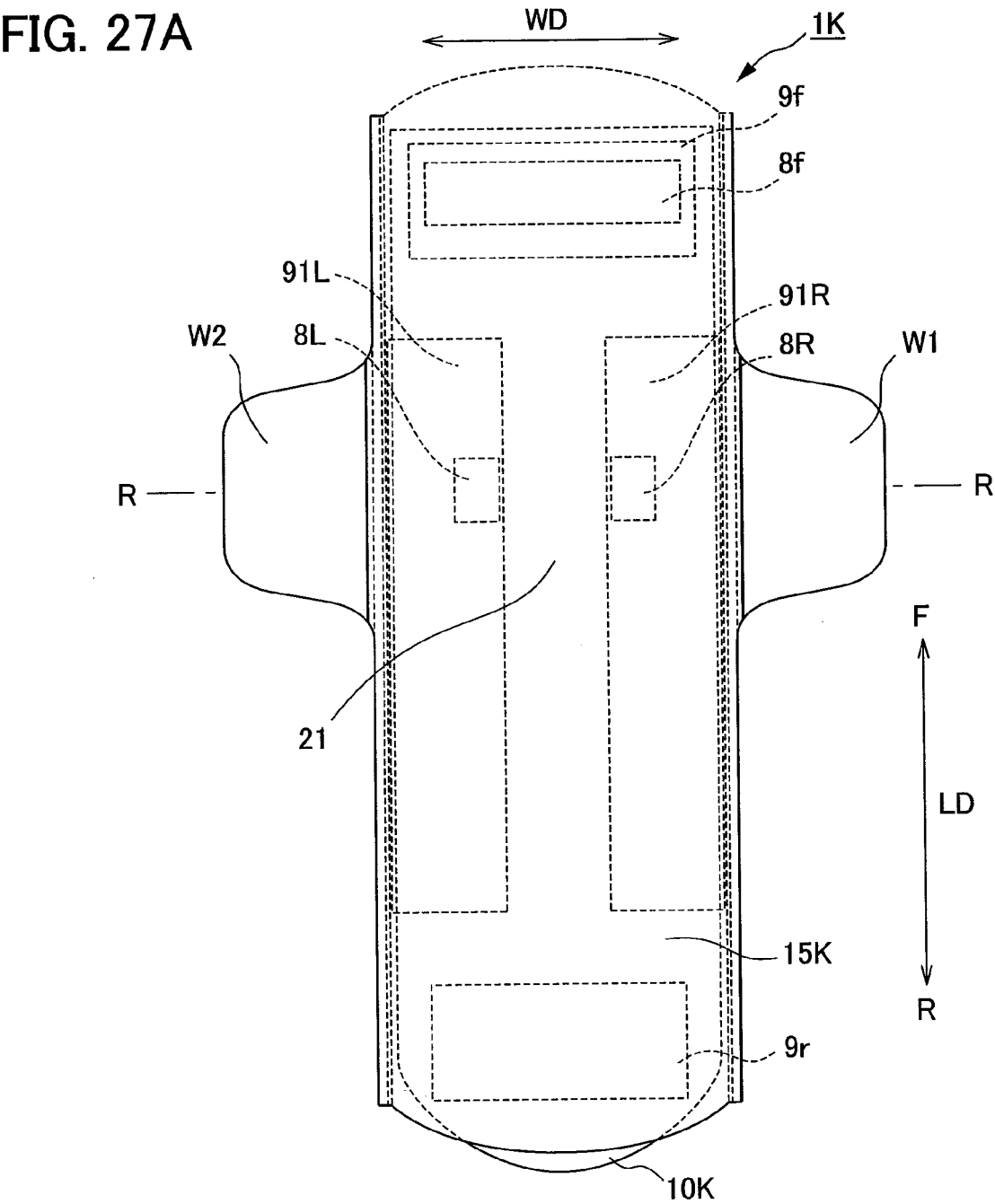

ABSORBENT ARTICLE

RELATED APPLICATIONS

The present application is based on International Application Number PCT/JP2007/061205 filed Jun. 1, 2007, and claims priority from Japanese Application Number 2006-155115 filed Jun. 2, 2006, the disclosures of which are hereby incorporated by reference herein in their entirety.

TECHNICAL FIELD

The present invention relates to an absorbent article.

BACKGROUND ART

Sanitary napkins, panty liners, urine-absorbing pads, and the like have conventionally been used as an absorbent article for absorbing excrement such as menstrual blood. These absorbent articles have an absorbent core for absorbing and holding menstrual blood or the like, a liquid permeable top sheet that covers the surface on a skin contacting surface of the absorbent core, and a liquid impermeable back sheet that covers the back corresponding to the clothing side of the absorbent core. For example, these absorbent articles can be adhered to the internal surface of a crotch piece of underwear.

Incidentally, in order to trap the excrement such as menstrual blood, it is desired that the abovementioned absorbent articles be used in a state where the absorption layer having the absorbent body is in contact with the excretory part of a wearer. However, in recent years, lifestyles of wearers have diversified, and with this, modes of usage of absorbent articles have followed in diversifying. For example, an absorbent article with improved adhesion to a wearer's body, and an absorbent article giving a less oppressive feeling due to the adhesion, for example, while maintaining leak-proof properties are demanded.

On the other hand, for example, Japanese Utility Model Application Publication No. Hei 03-101933 (hereinafter referred to as Patent Document 1) discloses an absorbent article having improvements in adhesion (adhesive properties) of the absorbent article to the wearer's body while wearing underwear. More specifically, flexible flaps are formed on both ends in the longitudinal direction of the absorbent article, and retainers provided at the flaps can be adhered to the underwear.

In addition, for example, Japanese Patent Application Publication No. Hei 11-99179 (hereinafter referred to as Patent Document 2) discloses an absorbent article having improvements in adhesion of the absorbent article to the wearer's body when underwear is put on; more specifically, flexible elastic members can be projected from both edge portions of a sanitary napkin, and an adhesive region is formed on a contact surface with the underwear located at the portion so projected, and then adhered to the underwear or the like.

Each of the absorbent articles as disclosed in Patent Documents 1 and 2 is provided with the elastic portions on both ends of the absorbent article in the longitudinal direction, and adapted to improve adhesion by pulling the absorbent article toward the excretory part of the wearer by the elastic force generated in the elastic members.

Furthermore, for example, Japanese Patent Application Publication No. 2005-95510 (hereinafter referred to as Patent Document 3) discloses an absorbent article having a hole or a guide portion through which a belt passes, where the belt has a fixing portion in each end, for fixing the belt to a top sheet and the like of the absorbent article.

The absorbent articles disclosed in Patent Document 3 is intended to prevent absorbent article dislocation and the like by providing a belt passing through a hole or a guide portion provided on a back surface sheet of the absorbent article.

DISCLOSURE OF THE INVENTION

Problems to be Solved by the Invention

However, the art disclosed in Patent Documents 1 to 3 has the ability to improve a predetermined adhesion of the absorbent article, for example, but could not change conformability of the absorbent article. Therefore, an absorbent article is demanded that can change the conformability of the absorbent article and the wearer's body while maintaining predetermined leak-proof properties.

The present invention has been made in view of the foregoing problem, and aims at providing an absorbent article that can change the conformability while maintaining predetermined leak-proof properties.

Means for Solving the Problems

To achieve the above objective, the present inventors have achieved the present invention based on the discovery that, by providing a belt-shaped member that can be stretched in a longitudinal direction and in a width direction on an absorbent article main body, and by joining the belt-shaped member with the absorbent article main body at a predetermined location, an absorbent article can be deformed along with expansion and contraction of the belt-shaped member. More specifically, the following kind of absorbent article is provided.

In a first aspect of the present invention, an absorbent article having a substantially elongated shape includes: an absorbent article main body at least including a top sheet portion that is at least partially liquid permeable and disposed on a first side in a thickness direction of the absorbent article, and a liquid retentive absorbent core portion being disposed at a side of a second side which is the other side of the first side in the thickness direction of the absorbent article, which is the second side of the top sheet portion; and a belt-shaped member disposed on the second side of the absorbent article main body, along a longitudinal direction of the absorbent article main body, in which the belt-shaped member has, in at least a part thereof, a deforming region that can deform so as to be narrower in a width direction of the belt-shaped member, an engaging portion that is provided in at least one end side of both ends in the longitudinal direction of the belt-shaped member, and the absorbent article main body and the belt-shaped member are joined with each other by joining portions provided in the deforming region spaced a predetermined distance apart from each other across a center in the width direction of the absorbent article main body.

According to the first aspect of the present invention, the absorbent article includes an absorbent article main body at least including a top sheet portion that is at least partially liquid permeable and disposed on a first side in a thickness direction of the absorbent article, and a liquid retentive absorbent core portion being disposed at a side of a second side which is the other side of the first side in the thickness direction of the absorbent article, which is the second side of the top sheet portion and a belt-shaped member disposed on the second side of the absorbent article main body, along a longitudinal direction of the absorbent article main body, and is formed to be substantially elongated. The belt-shaped member has, in at least a part thereof, a deforming region that can deform so as to narrow in a width direction. In addition, an engaging portion is provided in at least one end side in the longitudinal direction of the belt-shaped member. Moreover, an absorbent article can be provided in which the absorbent article main body and the belt-shaped member are joined with each other in the deforming region, by joining portions spaced a predetermined distance apart from each other across a center in the width direction of the absorbent article main body.

According to a second aspect of the present invention, in the absorbent article as described in the first aspect, the deforming region can expand and contract in the longitudinal direction and in the width direction, deforms so as to narrow in the width direction in association with expansion in the longitudinal direction, and deforms so as to widen in the width direction in association with contraction in the longitudinal direction.

According to the second aspect of the present invention, the deforming region is formed so as to be able to expand and contract in the longitudinal direction and in the width direction. For example, the deforming region narrows in the width direction, in accordance with the belt-shaped member being pulled in the longitudinal direction. In addition, by weakly pulling the belt-shaped member in the longitudinal direction, the deforming region narrows in the width direction to a degree in accordance therewith. Thus, an absorbent article can be provided in which a degree of deformation in the thickness direction of the absorbent article can be adjusted, in accordance with a degree of deformation of the deforming region in the width direction.

According to a third aspect of the present invention, in the absorbent article as described in the first or the second aspect, a grip portion, of which at least a part projects from an outer peripheral portion in the longitudinal direction of the absorbent article main body, is formed at least in one end side in the longitudinal direction of the belt-shaped member.

According to the third aspect of the present invention, an absorbent article can be provided that includes a grip portion, which projects from an outer peripheral portion in the longitudinal direction of the absorbent article main body, in at least one end side in the longitudinal direction.

According to a fourth aspect of the present invention, in the absorbent article as described in any one of the first to the third aspects, a cover member is further provided on the second side of the absorbent article main body, which encapsulates at least a part in the longitudinal direction of the belt-shaped member and an entirety in the width direction of the belt-shaped member.

According to the fourth aspect of the present invention, the absorbent article can be provided, including, on the second side in the thickness direction, a cover member for encapsulating the belt-shaped member.

According to a fifth aspect of the present invention, in the absorbent article of any one of the first to fourth aspects, the grip portion has a guiding element for implying an expansion direction of the belt-shaped member.

According to the fifth aspect of the present invention, an absorbent article can be provided, having a guiding element on the grip portion, for implying an expansion direction of the belt-shaped member.

According to a sixth aspect of the present invention, in the absorbent article of any one of the first to fifth aspects, the belt-shaped member includes at least one portion that is a liquid impermeable material.

According to the sixth aspect of the present invention, an absorbent article can be provided, in which the belt-shaped member has at least one portion that is a liquid impermeable material.

According to a seventh aspect of the present invention, in the absorbent article of any one of the first to the sixth aspects, a length of the belt-shaped member in a width direction is at least 30% of a length of the absorbent article main body in the width direction.

According to the seventh aspect of the present invention, an absorbent article can be provided, in which a length of the belt-shaped member in a width direction is at least 30% of a length of the absorbent article main body in the width direction.

According to an eighth aspect of the present invention, in the absorbent article of any one of the first to the seventh aspects, the joining portions are brought together by deforming the deforming region so as to narrow in the width direction, and the absorbent article main body is deformed to be convex to the first side.

According to the eighth aspect of the present invention, an absorbent article can be provided in which an absorbent article main body can be deformed into a convex shape to one side in a thickness direction, by the absorbent article main body deforming so as to narrow in the width direction of the deforming region.

According to a ninth aspect of the present invention, in the absorbent article of any one of the second to the eighth aspects, a projecting height of the convex deformation of the absorbent article main body can be adjusted, by adjusting an expansion degree of the deforming region in the longitudinal direction thereby adjusting the distance between the joining portions.

According to the ninth aspect of the present invention, an absorbent article can be provided, in which the projecting height of the convex deformation of the absorbent article main body in the thickness direction can be adjusted, by adjusting an expansion degree of the deforming region in the longitudinal direction.

In a tenth aspect of the present invention, an absorbent article having a substantially elongated shape includes: an absorbent article main body at least including a top sheet portion that is at least partially liquid permeable and disposed on a first side in a thickness direction of the absorbent article, and a liquid retentive absorbent core portion being disposed at a side of a second side, which is the other side of the first side in the thickness direction of the absorbent article, which is the second side of the top sheet portion; and a belt-shaped member disposed on the second side of the absorbent article main body along a longitudinal direction of the absorbent article main body, having at least in part a deforming region that can be deformed so as to narrow in the width direction in association with expansion in the longitudinal direction; and the joining portions for joining the belt-shaped member with the absorbent article main body, provided in the deforming region, and spaced a predetermined distance apart from each other across a center in the width direction of the absorbent article main body, in which the deforming region is deformed so as to expand in the longitudinal direction while narrowing in the width direction, by pulling the belt-shaped member in the longitudinal direction, the joining portions approach each other by a deformation in the deforming region, and the absorbent article main body deforms to be convex to the first side.

According to the tenth aspect of the present invention, the absorbent article includes: an absorbent article main body at least including a top sheet portion that is at least partially liquid permeable and disposed on a first side in a thickness direction of the absorbent article, and a liquid retentive absorbent core portion being disposed at a side of a second side, which is the other side of the first side in the thickness direction of the absorbent article, which is the second side of the top sheet portion; a belt-shaped member disposed on the second side of the absorbent article main body along a longitudinal direction of the absorbent article main body, having at least in part a deforming region that can be deformed so as to narrow in the width direction in association with expansion in the longitudinal direction; and joining portions for joining the belt-shaped member with the absorbent article main body, provided in the deforming region, and spaced a predetermined distance apart from each other across a center in the width direction of the absorbent article main body. Moreover, the deforming region is deformed so as to expand in the longitudinal direction while narrowing in the width direction, by pulling the belt-shaped member in the longitudinal direction. The joining portions are brought together by deforming these deforming regions, and an absorbent article can be provided in which an absorbent article main body is deformed to be convex to the first side.

In an eleventh aspect of the present invention, an absorbent article having a substantially elongated shape includes: an absorbent article main body at least including a top sheet portion that is at least partially liquid permeable and disposed on a first side in a thickness direction of the absorbent article, and a liquid retentive absorbent core portion being disposed at a side of a second side which is the other side of the first side in the thickness direction of the absorbent article, which is the second side of the top sheet portion; and a belt-shaped member disposed on the second side of the absorbent article main body, along a longitudinal direction of the absorbent article main body, in which: the absorbent article main body includes joining portions spaced a predetermined distance apart from each other across a center in the width direction of the absorbent article main body; the joining portions have a connecting member for connecting each of the joining portions; and the belt-shaped member is connected in a first end side in the longitudinal direction thereof, to each of the joining portions via the connecting member.

According to the eleventh aspect of the present invention, an absorbent article includes: an absorbent article main body at least including a top sheet portion that is at least partially liquid permeable and disposed on a first side in a thickness direction of the absorbent article, and a liquid retentive absorbent core portion being disposed at a side of a second side which is the other side of the first side in the thickness direction of the absorbent article, which is the second side of the top sheet portion; and a belt-shaped member disposed on a second side of the absorbent article main body, along a longitudinal direction of the absorbent article main body. Furthermore, the absorbent article main body includes joining portions spaced a predetermined distance apart from each other across a center in the width direction of the absorbent article main body, each of the joining portions being joined by a connecting member. An absorbent article can be provided in which the belt-shaped member is connected in a first end side in the longitudinal direction thereof, to each of the joining portions via the connecting member.

According to a twelfth aspect of the present invention, in the absorbent article as described in the eleventh aspect, a grip portion, of which at least a part projects from an outer peripheral portion of the absorbent article main body in the longitudinal direction, is formed in a second end side, which is opposite to the first end side, in the longitudinal direction of the belt-shaped member.

According to the twelfth aspect of the present invention, an absorbent article can be provided in which a grip portion, of which at least a part projects from an outer peripheral portion of the absorbent article main body in the longitudinal direction, is formed in a second end side, which is opposite to the first end side, in the longitudinal direction of the belt-shaped member.

According to a thirteenth aspect of the present invention, in the absorbent article of the eleventh or the twelfth aspect, a cover member is further provided on the second side of the absorbent article main body, which encapsulates at least a part in the longitudinal direction of the belt-shaped member and an entirety in the width direction of the belt-shaped member.

According to the thirteenth aspect of the present invention, the absorbent article can be provided, in which a cover member is further provided on the second side of the absorbent article main body, which encapsulates at least a part in the longitudinal direction of the belt-shaped member and an entirety in the width direction of the belt-shaped member.

According to a fourteenth aspect of the present invention, in the absorbent article of any one of the eleventh to the thirteenth aspects, the grip portion has a guiding element for implying an expansion direction of the belt-shaped member.

According to the fourteenth aspect of the present invention, an absorbent article can be provided, having a guiding element on the grip portion, for implying an expansion direction of the belt-shaped member.

According to a fifteenth aspect of the present invention, in the absorbent article of any one of the eleventh to the fourteenth aspects, a length of the belt-shaped member in a width direction is at least 30% of a length of the absorbent article main body in a width direction.

According to the fifteenth aspect of the present invention, an absorbent article can be provided in which a length of the belt-shaped member in a width direction is in a range of at least 30% of a length of the absorbent article main body in a width direction.

According to a sixteenth aspect of the present invention, in the absorbent article of any one of the eleventh to the fifteenth aspects, the joining portions are brought together by deforming the deforming region so as to narrow in the width direction, and the absorbent article main body is deformed to be convex to the first side.

According to the sixteenth aspect of the present invention, an absorbent article can be provided in which, by deforming the deforming region so as to narrow a length in the width direction, the joining portions are brought together, and the absorbent article main body is made to deform to be convex to one side.

According to a seventeenth aspect of the present invention, in the absorbent article of any one of the eleventh to the sixteenth aspects, a projecting height of the convex deformation of the absorbent article main body can be adjusted, by adjusting a position of the belt-shaped member with respect to the absorbent article main body in the longitudinal direction, thereby adjusting a distance between the joining portions.

According to the seventeenth aspect of the present invention, an absorbent article can be provided in which a projecting height of the convex deformation of the absorbent article main body can be adjusted, by adjusting a position of the belt-shaped member with respect to the absorbent article main body in the longitudinal direction, thereby adjusting a distance between the joining portions.

Effects of the Invention

According to the present invention, an absorbent article can be provided, that can change the conformability of the absorbent article while maintaining predetermined leak-proof properties.

BRIEF DESCRIPTION OF THE DRAWINGS

FIG. 23 is a front view of a sanitary napkin according to a ninth embodiment of the present invention;

FIG. 27A is a front view of a sanitary napkin according to a twelfth embodiment of the present invention;

PREFERRED MODE FOR CARRYING OUT THE INVENTION

Embodiments of the present invention are described hereinafter with reference to the accompanying drawings. Moreover, it is to be understood that the embodiments of the present invention are not limited thereto, and the technical scope of the present invention is not limited thereto.

In addition, although the absorbent articles according to the present invention are positioned on the crotch of the human body in order to absorb menstrual blood, urine, and leukorrhea discharged from the human body, the following preferred embodiments are directed to sanitary napkins, the primary object of which is to absorb menstrual blood discharged from the vaginal opening of females. In addition, one of the two surfaces of the absorbent article that is directed to the excretory part is called a "skin contacting side" and the other is called a "skin noncontacting side", irrespective of whether or not clothing is worn on the outside thereof.

Figure 1:
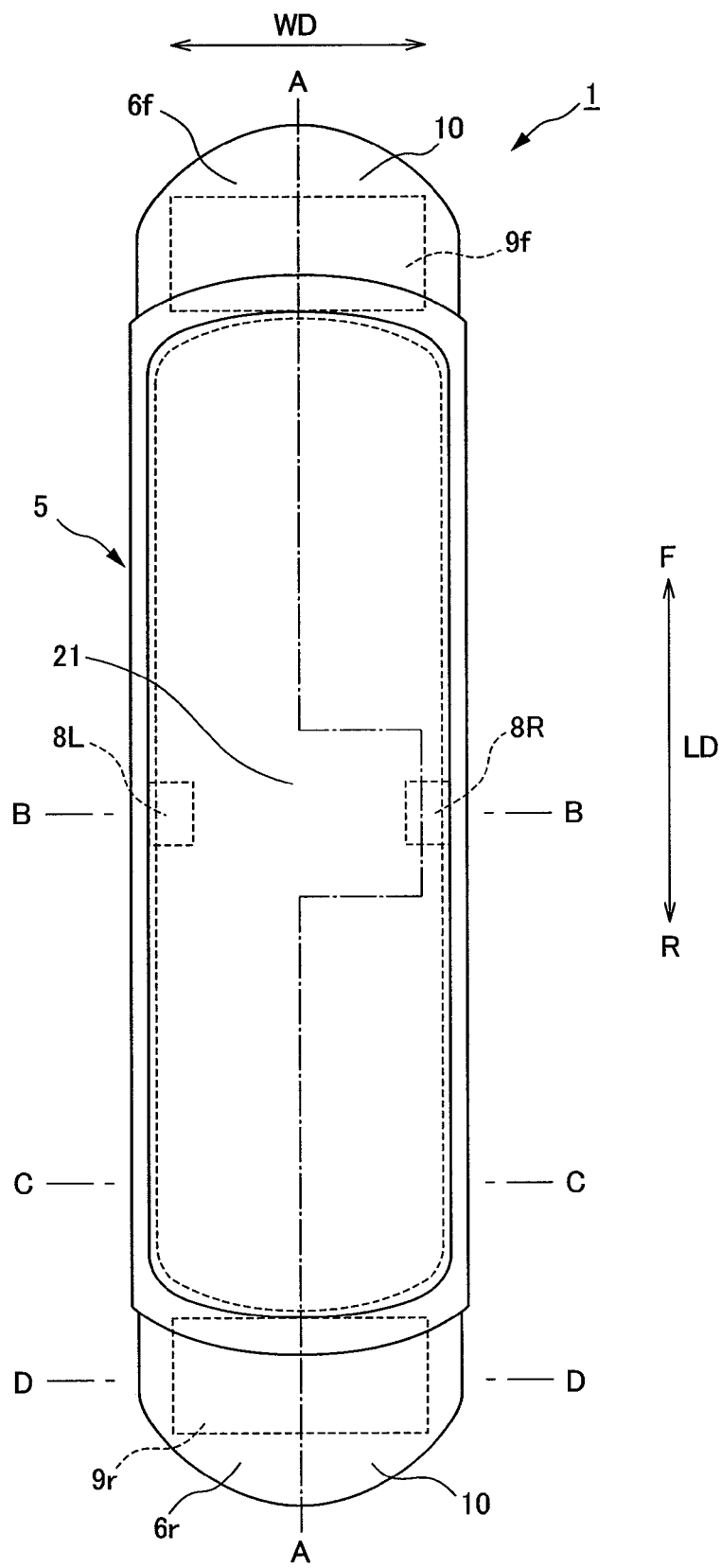
FIG. 1 is a front view of a sanitary napkin according to a first embodiment of the present invention.
Figure 2:
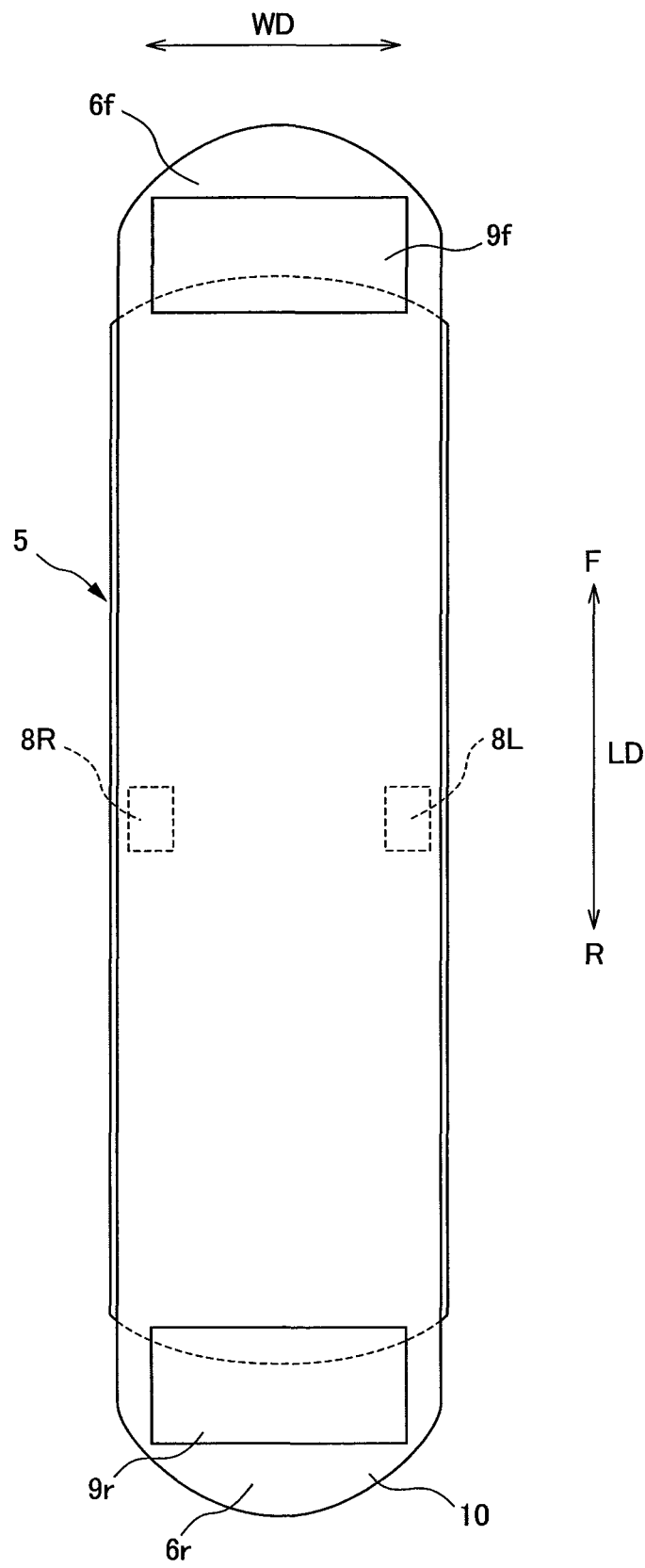
FIG. 2 is a back view of FIG. 1.
Figure 3:
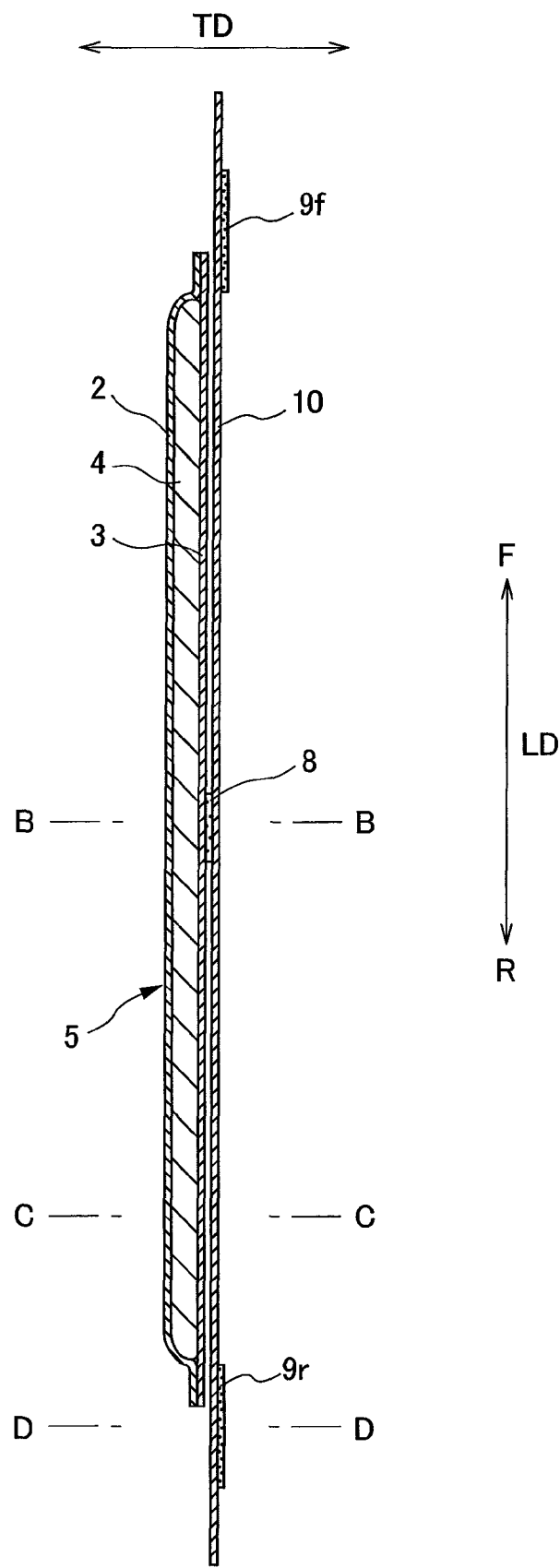
FIG. 3 is a sectional view taken along the line A-A of FIG. 1.
Figure 4A:
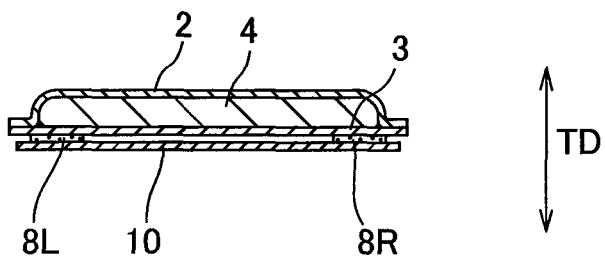
FIG. 4A is a sectional view taken along the line B-B of FIG. 1.
Figure 4B:
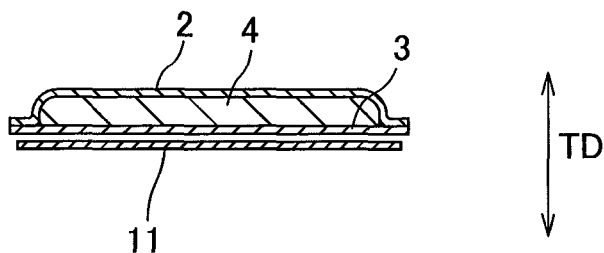
FIG. 4B is a sectional view taken along the line C-C of FIG. 1.
Figure 4C:
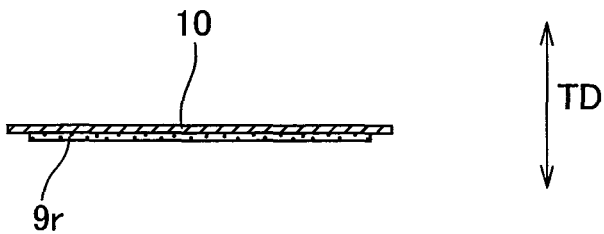
FIG. 4C is a sectional view taken along the line D-D of FIG. 1.
Figure 5A:
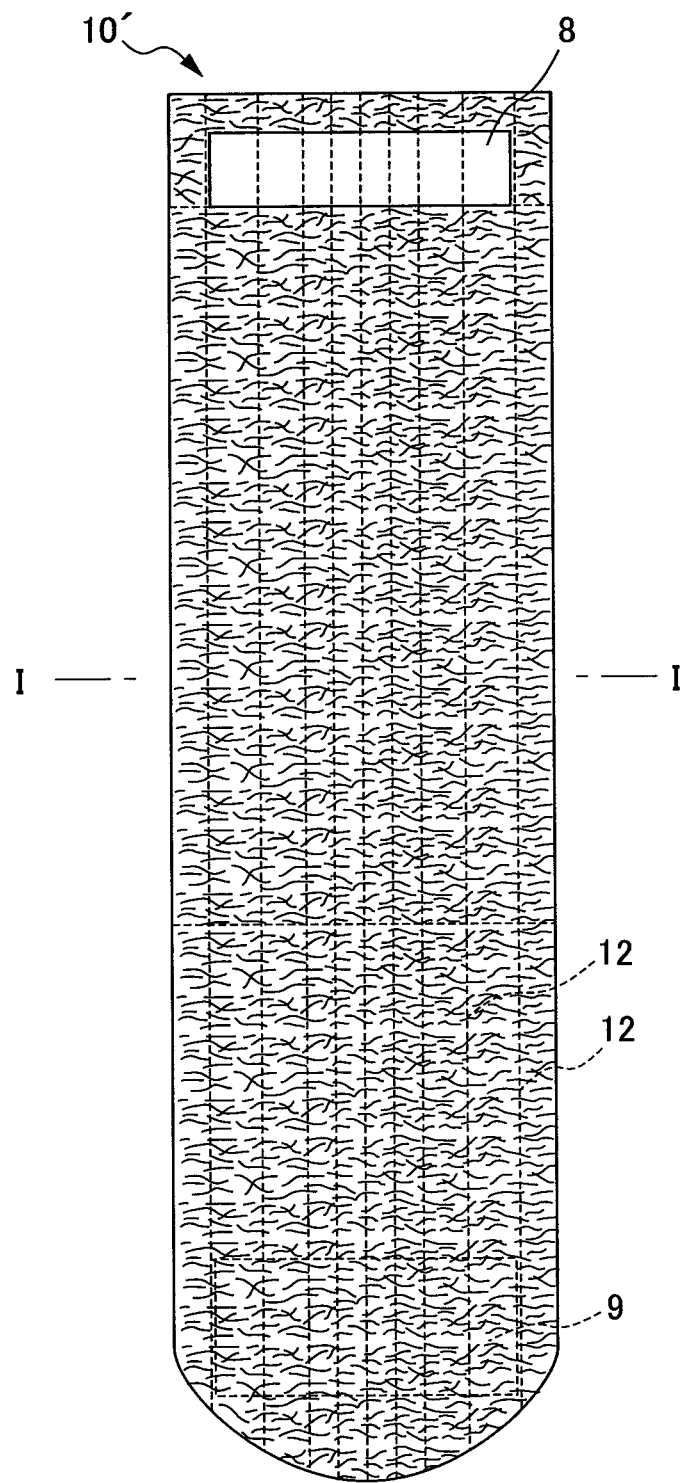
FIG. 5A is a front view of a belt-shaped member according to the first embodiment.
Figure 5B:
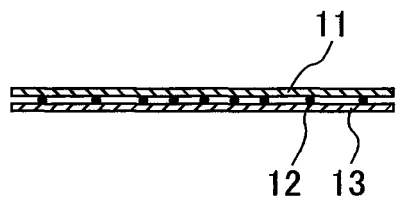
FIG. 5B is a sectional view taken along the line I-I of FIG. 5A.
Figure 6A:
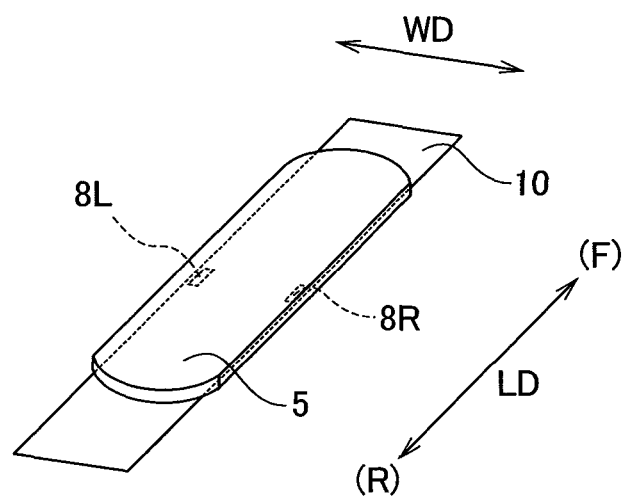
FIG. 6A is a perspective view illustrating a deformed state of the belt-shaped member according to the first embodiment.
Figure 6B:
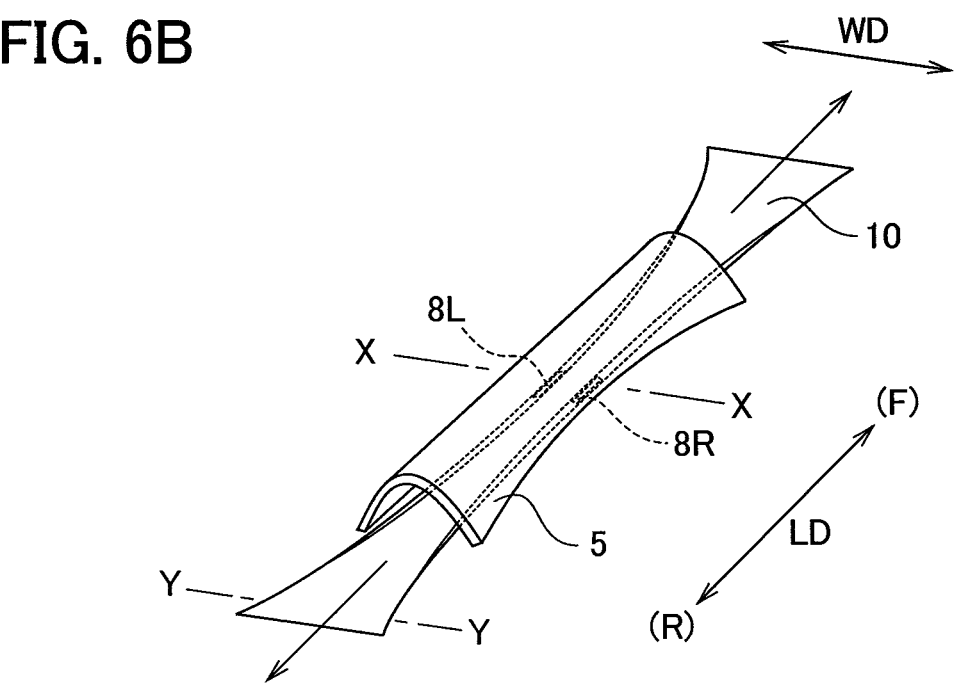
FIG. 6B is a perspective view showing the belt-shaped member of FIG. 6A in an expanded state.
Figure 6C:
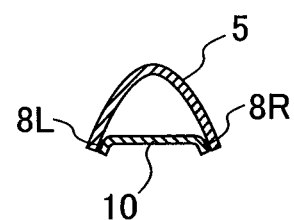
FIG. 6C is a sectional view taken along the line X-X in FIG. 6B.
Figure 6D:
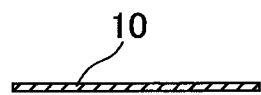
FIG. 6D is a sectional view taken along the line Y-Y in FIG. 6B.
Figure 7:
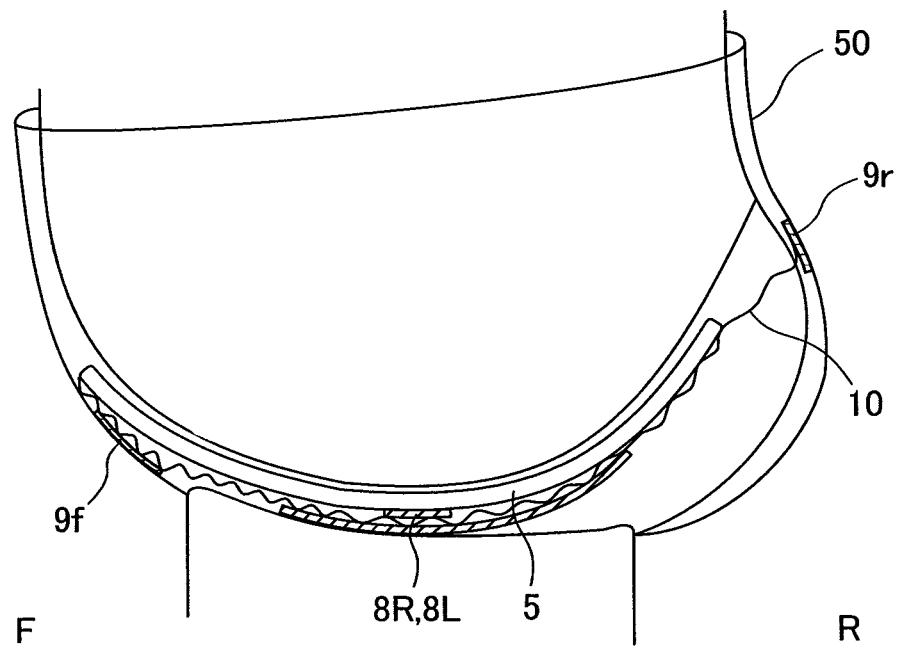
FIG. 7 is a diagram showing an attached state of the sanitary napkin according to the first embodiment.
Figure 8:
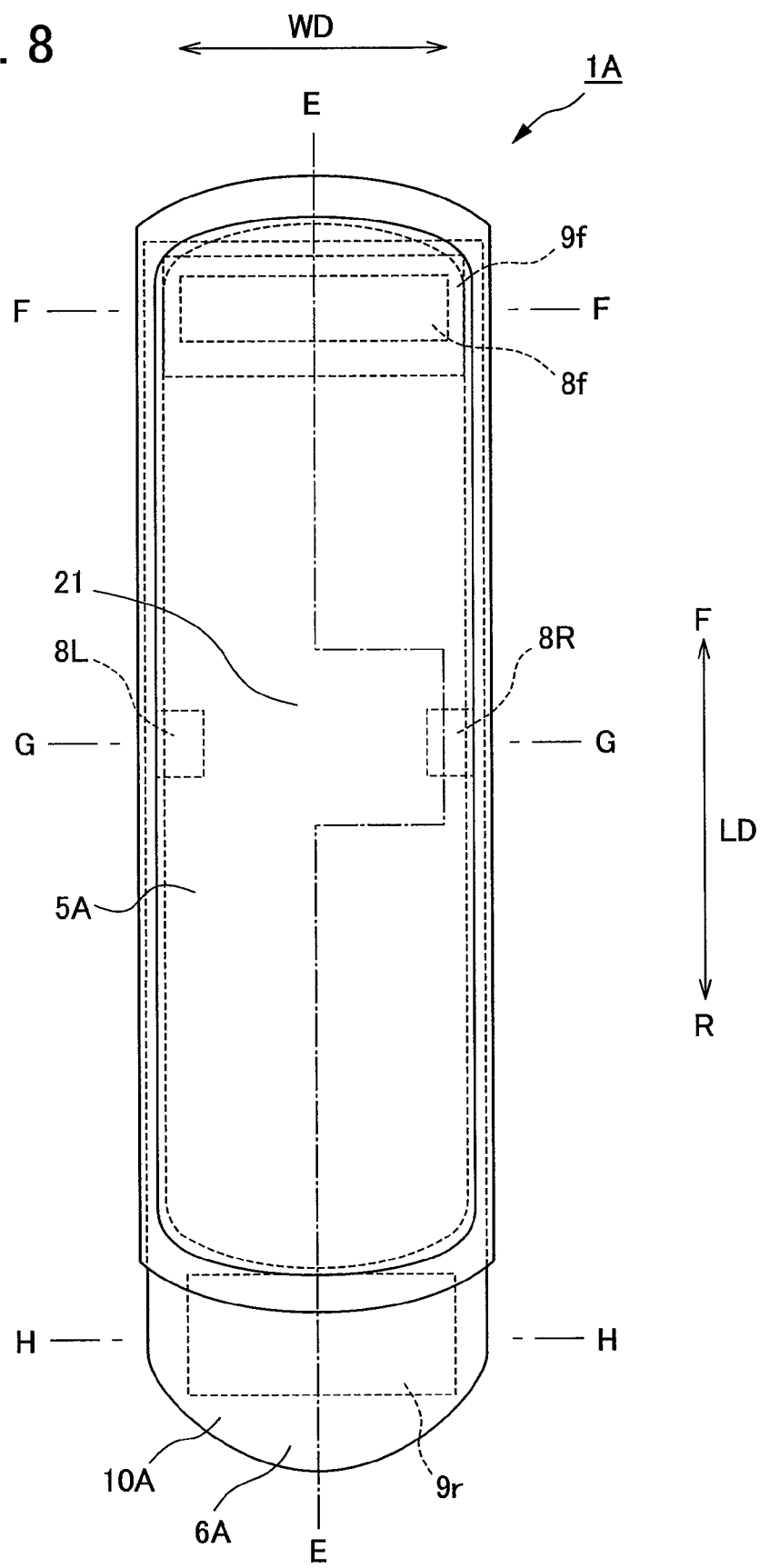
FIG. 8 is a front view of a sanitary napkin according to a second embodiment of the present invention.
Figure 9:
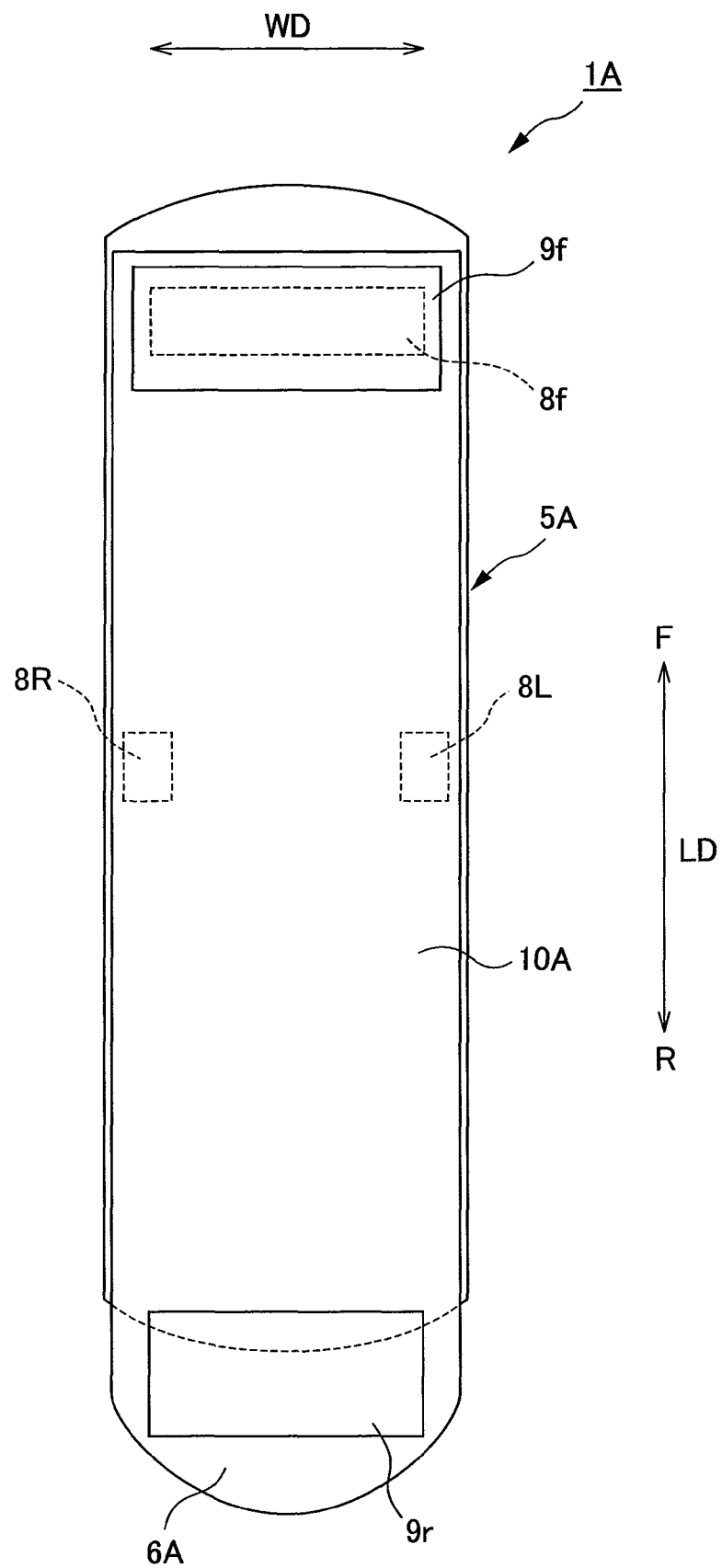
FIG. 9 is a back view of FIG. 8.
Figure 10:
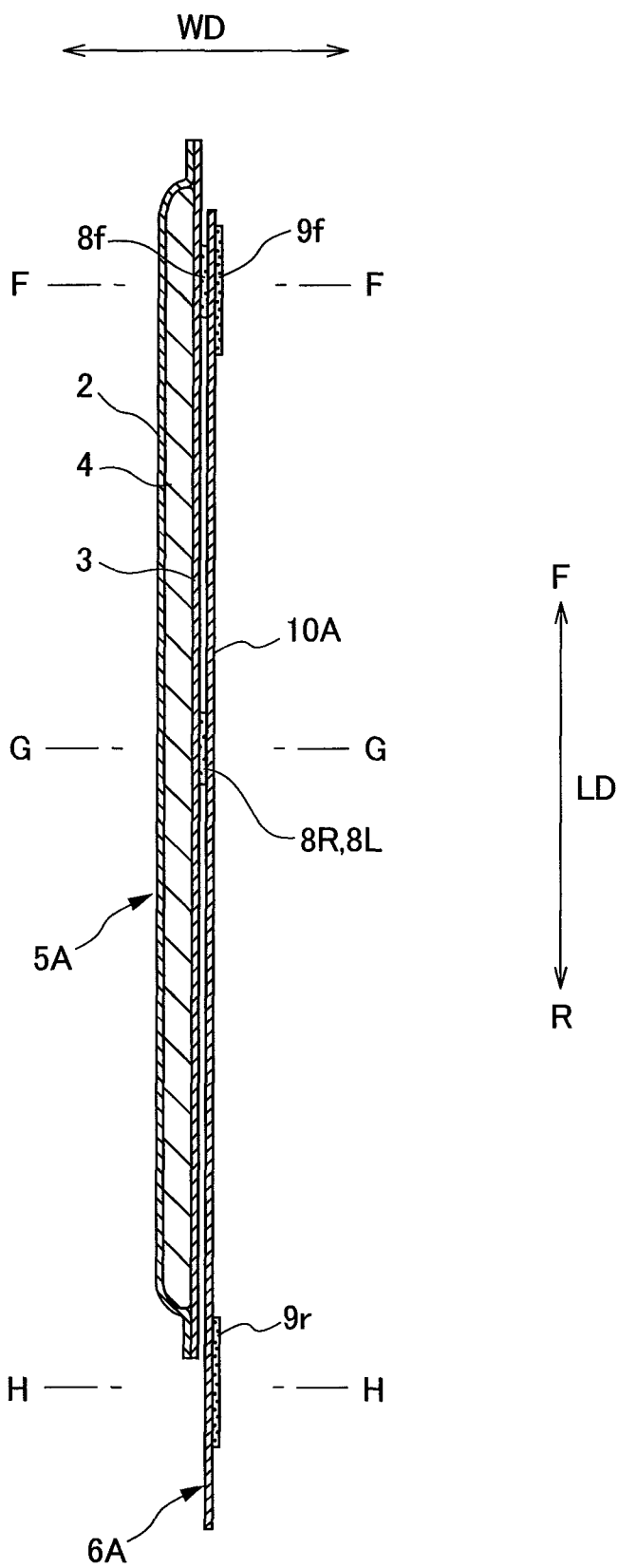
FIG. 10 is a sectional view taken along the line E-E of FIG. 8.

FIG. 1 is a front view of a sanitary napkin according to a first embodiment of the present invention. FIG. 2 is a back view of FIG. 1. FIG. 3 is a sectional view taken along the line A-A of FIG. 1. FIG. 4A is a sectional view taken along the line B-B of FIG. 1. FIG. 4B is a sectional view taken along the line C-C of FIG. 1. FIG. 4C is a sectional view taken along the line D-D of FIG. 1. FIG. 5A is a front view of a belt-shaped member according to the first embodiment. FIG. 5B is a sectional view taken along the line I-I of FIG. 5A. FIG. 6A is a perspective view showing a deformed state of the belt-shaped member according to the first embodiment. FIG. 6B is a perspective view showing the belt-shaped member of FIG. 6A in an expanded state. FIG. 6C is a sectional view taken along the line X-X in FIG. 6B. FIG. 6D is a sectional view taken along the line Y-Y in FIG. 6B. FIG. 7 is a diagram showing the attached state of the sanitary napkin according to the first embodiment. FIG. 8 is a front view of a sanitary napkin according to a second embodiment of the present invention. FIG. 9 is a back view of FIG. 8. FIG. 10 is a sectional view taken along the line E-E of FIG. 8.

Figure 11A:
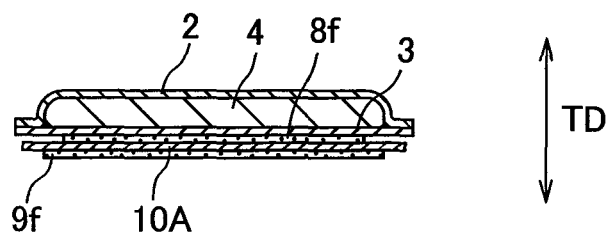
FIG. 11A is a sectional view taken along the line F-F of FIG. 8.
Figure 11B:
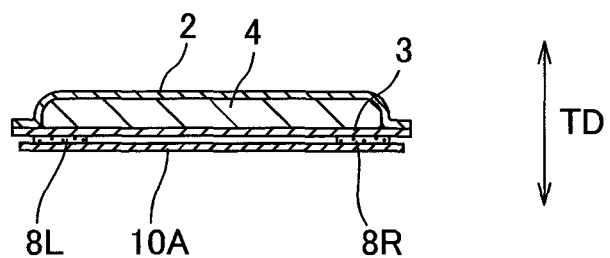
FIG. 11B is a sectional view taken along the line G-G of FIG. 8.
Figure 11C:
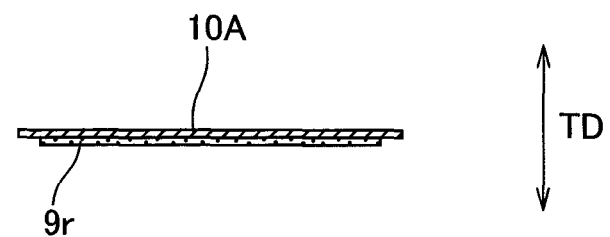
FIG. 11C is a sectional view taken along the line H-H of FIG. 8.
Figure 12A:
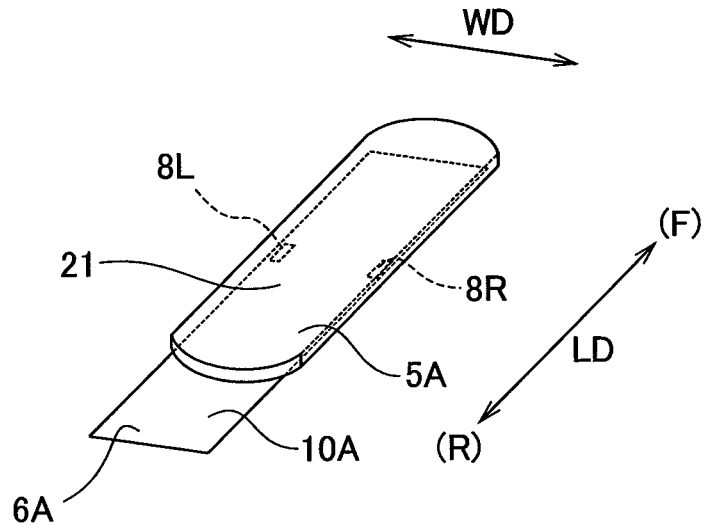
FIG. 12A is a perspective view showing a deformed state of a belt-shaped member according to the second embodiment.
Figure 12B:
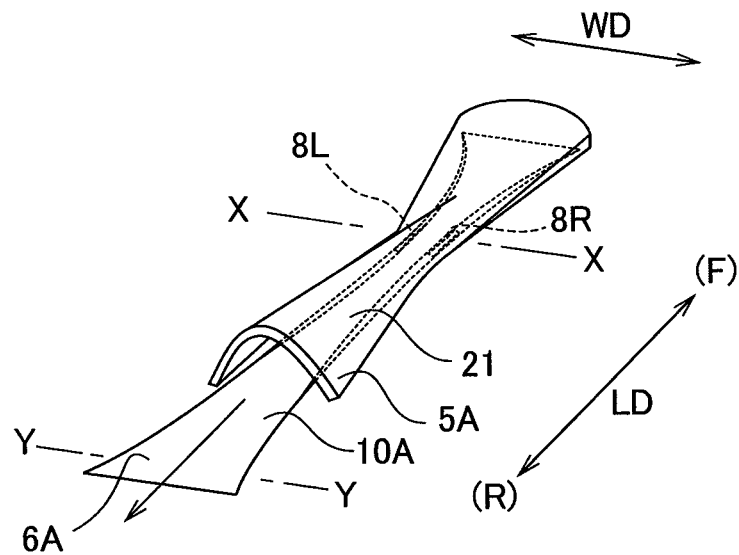
FIG. 12B is a perspective view showing an expanded state of a belt-shaped member according to the second embodiment.
Figure 12C:
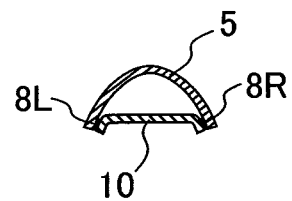
FIG. 12C is a sectional view taken along the line X-X of FIG. 12B.
Figure 12D:
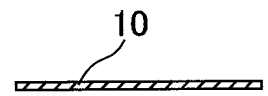
FIG. 12D is a sectional view taken along the line Y-Y of FIG. 12B.
Figure 13A:
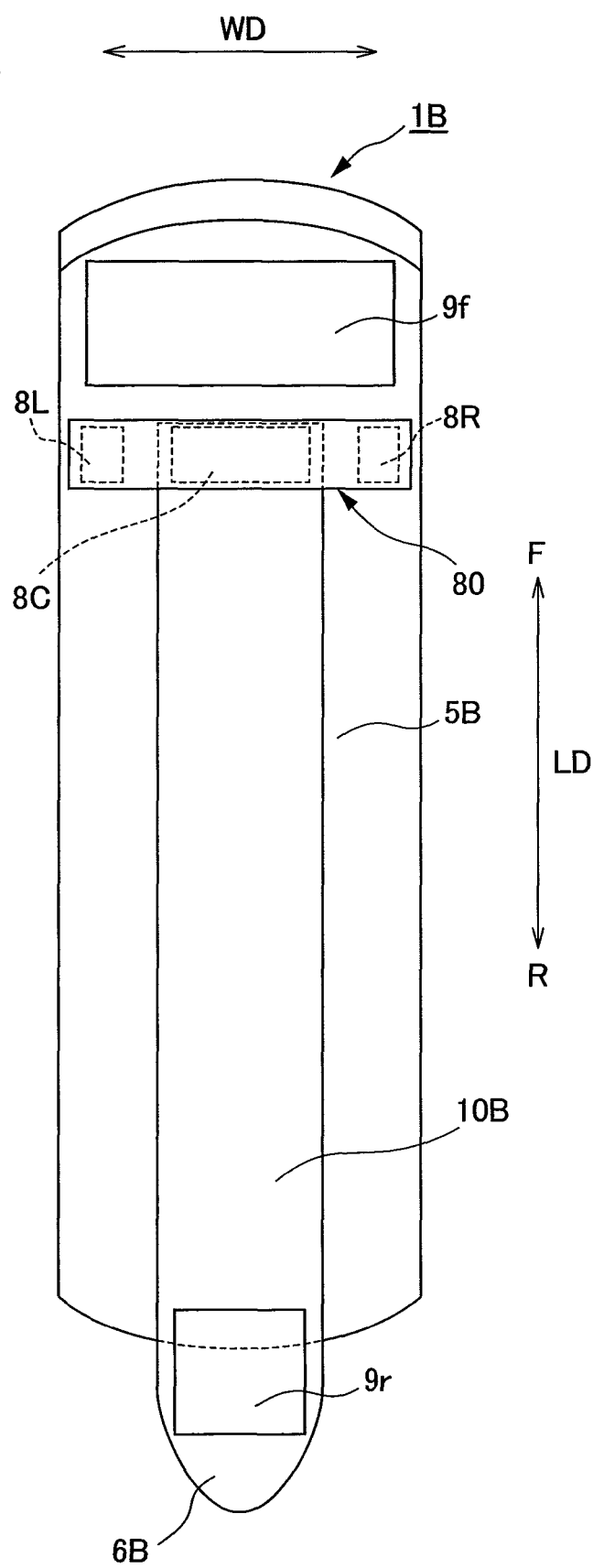
FIG. 13A is a back view of a sanitary napkin according to a third embodiment of the present invention.
Figure 13B:
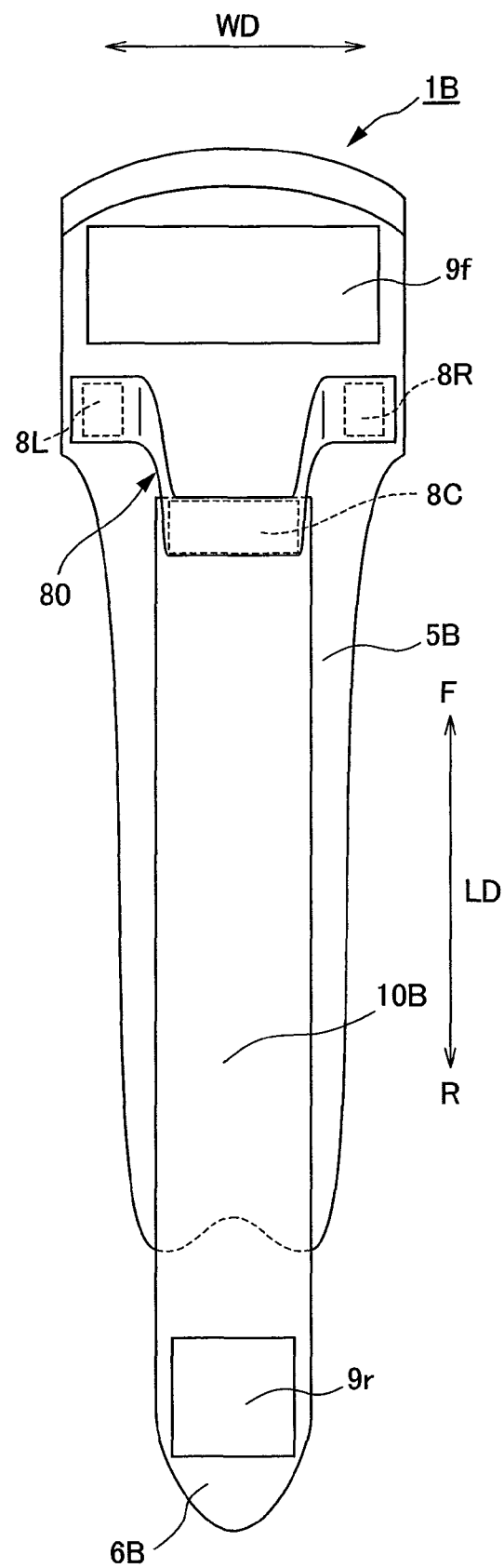
FIG. 13B is a back view showing an expanded state of the sanitary napkin according to the third embodiment.
Figure 14:
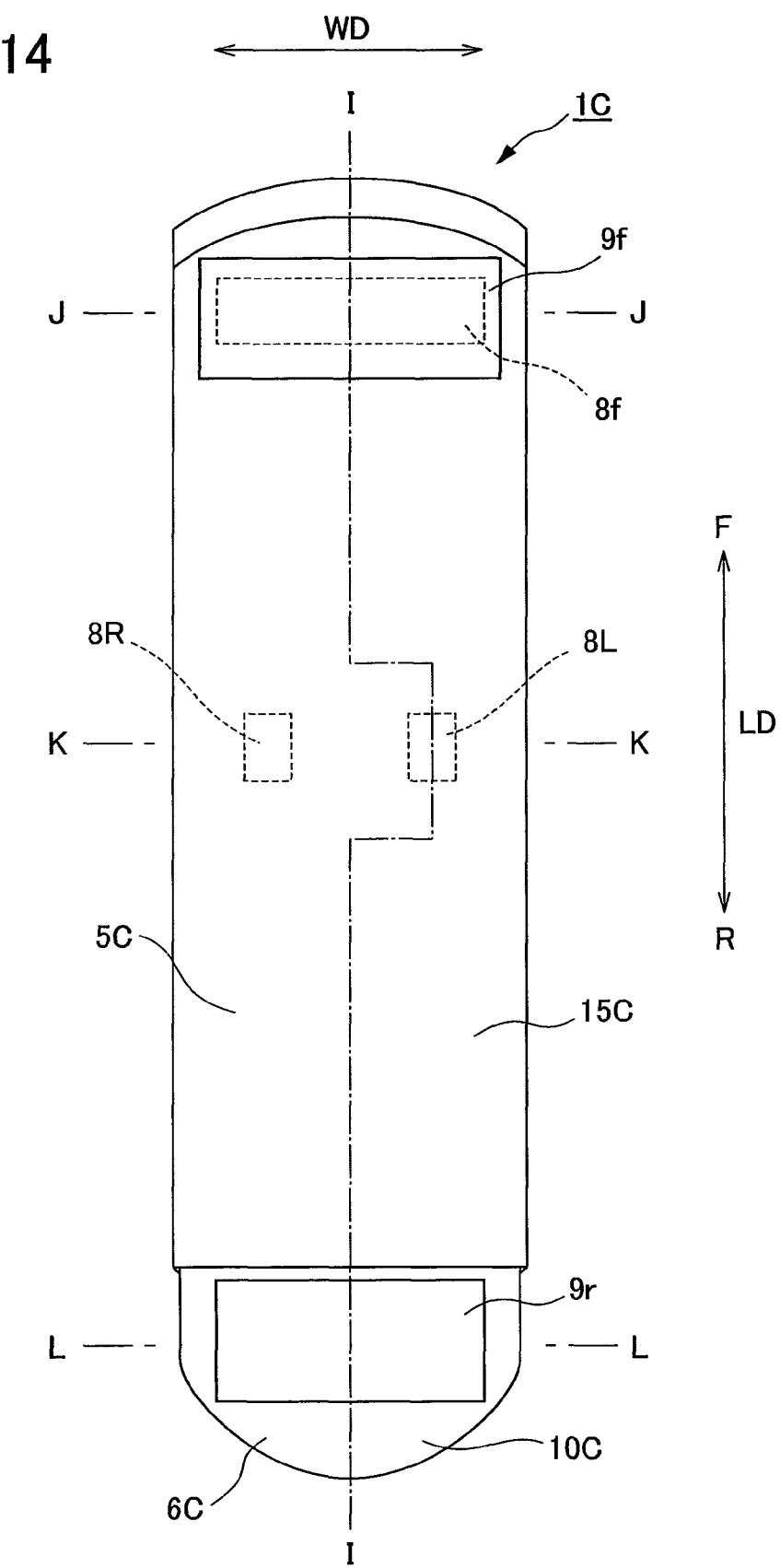
FIG. 14 is a front view of a sanitary napkin according to a fourth embodiment of the present invention.
Figure 15:
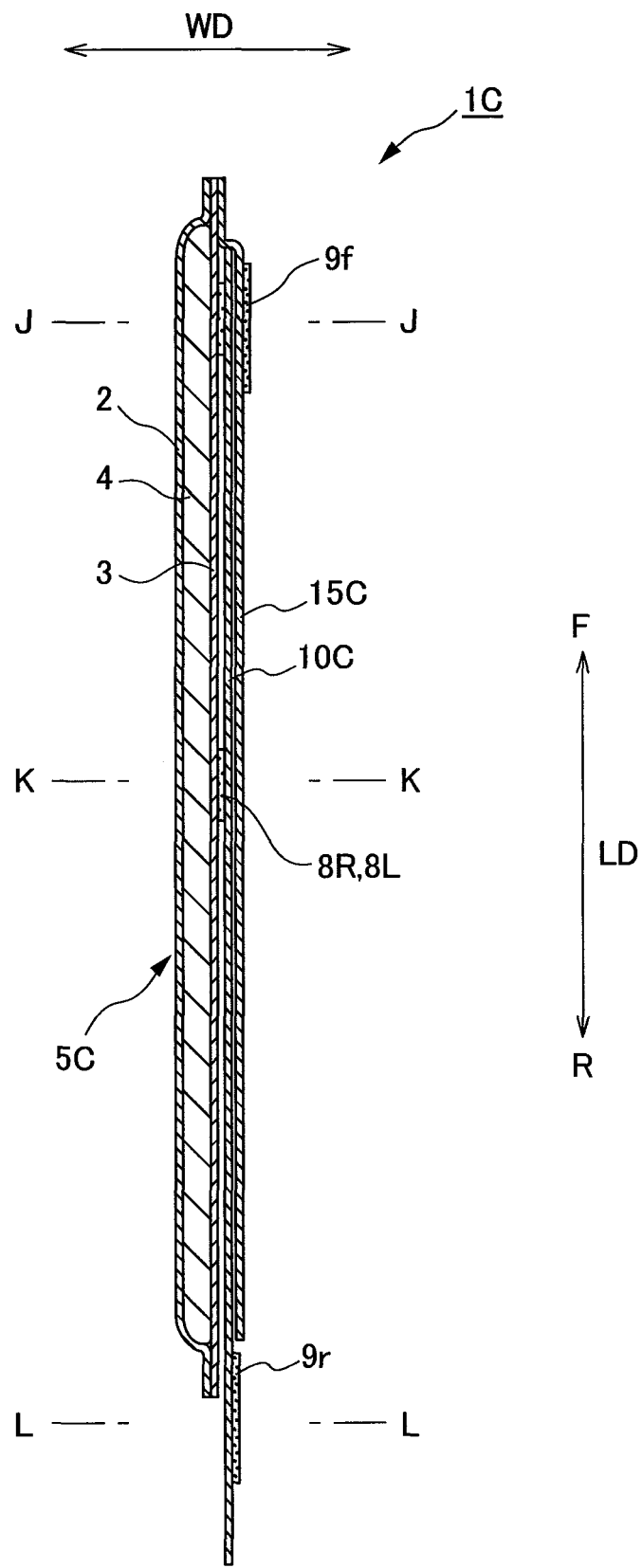
FIG. 15 is a sectional view taken along the line I-I of FIG. 14.
Figure 16A:
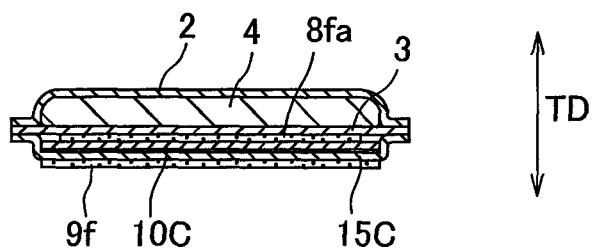
FIG. 16A is a sectional view taken along the line J-J of FIG. 14.
Figure 16B:
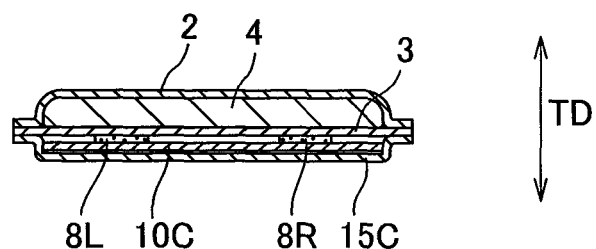
FIG. 16B is a sectional view taken along the line K-K of FIG. 14.
Figure 16C:
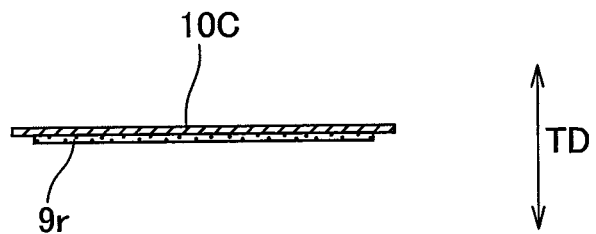
FIG. 16C is a sectional view taken along the line L-L of FIG. 14.
Figure 16D:
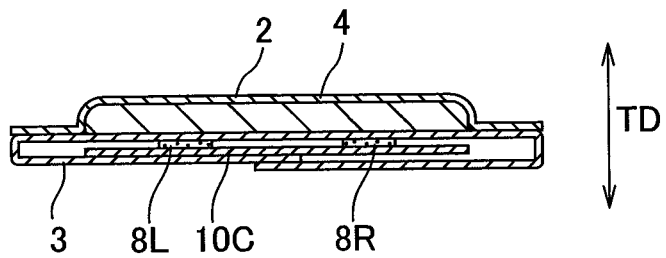
FIG. 16D is a diagram showing another configuration of FIG. 14.
Figure 17:
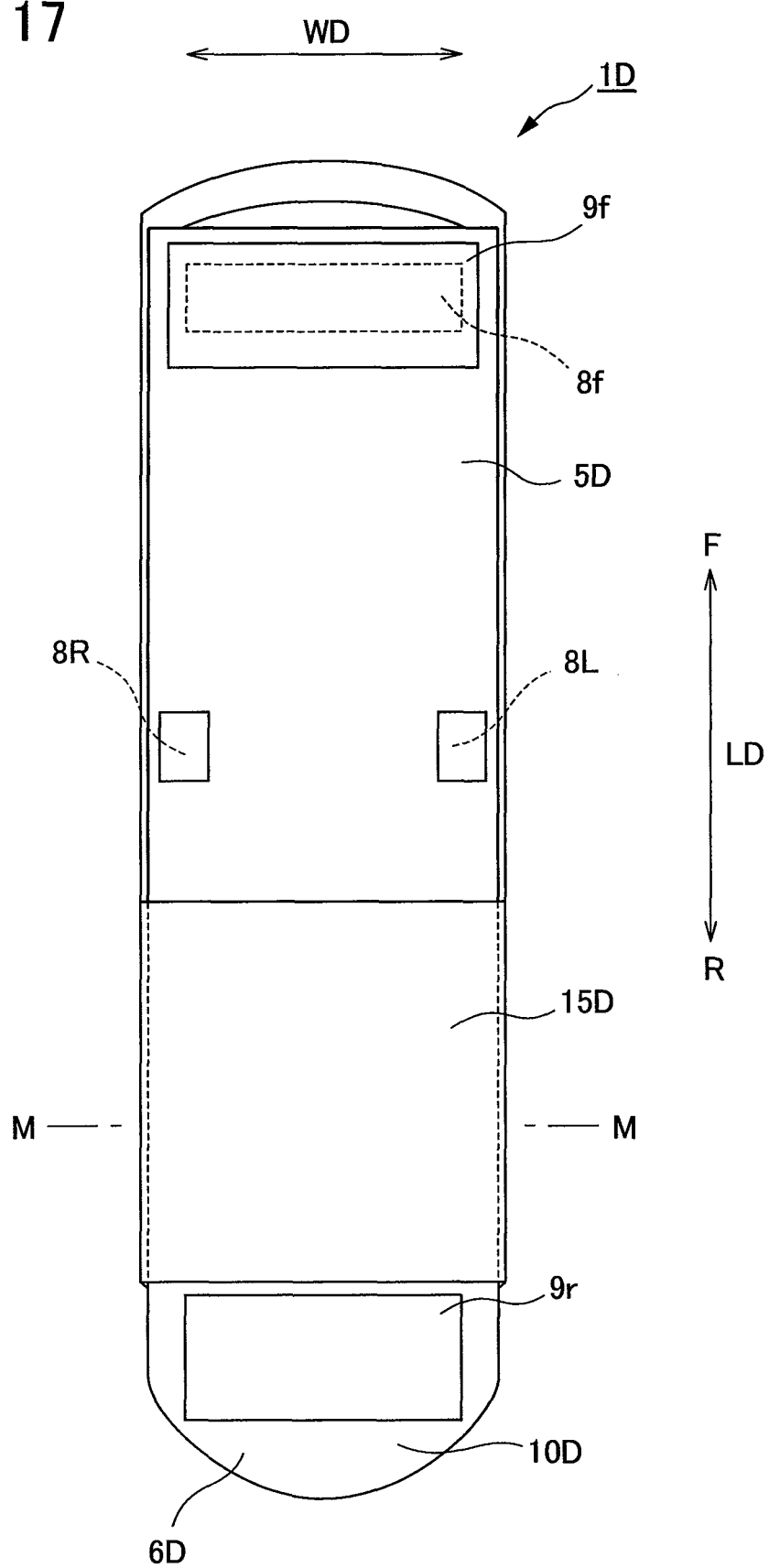
FIG. 17 is a back view of a sanitary napkin according to a fifth embodiment of the present invention.
Figure 18A:
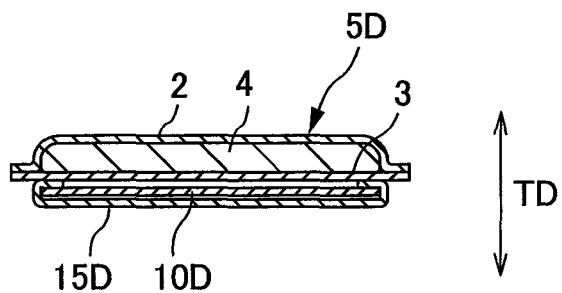
FIG. 18A is a sectional view taken along the line M-M of FIG. 17.
Figure 18B:
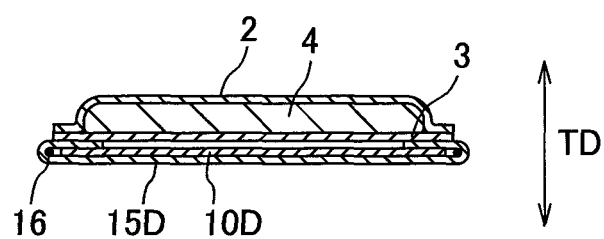
FIG. 18B is a sectional view taken along the line M-M according to another configuration of FIG. 17.
Figure 19A:
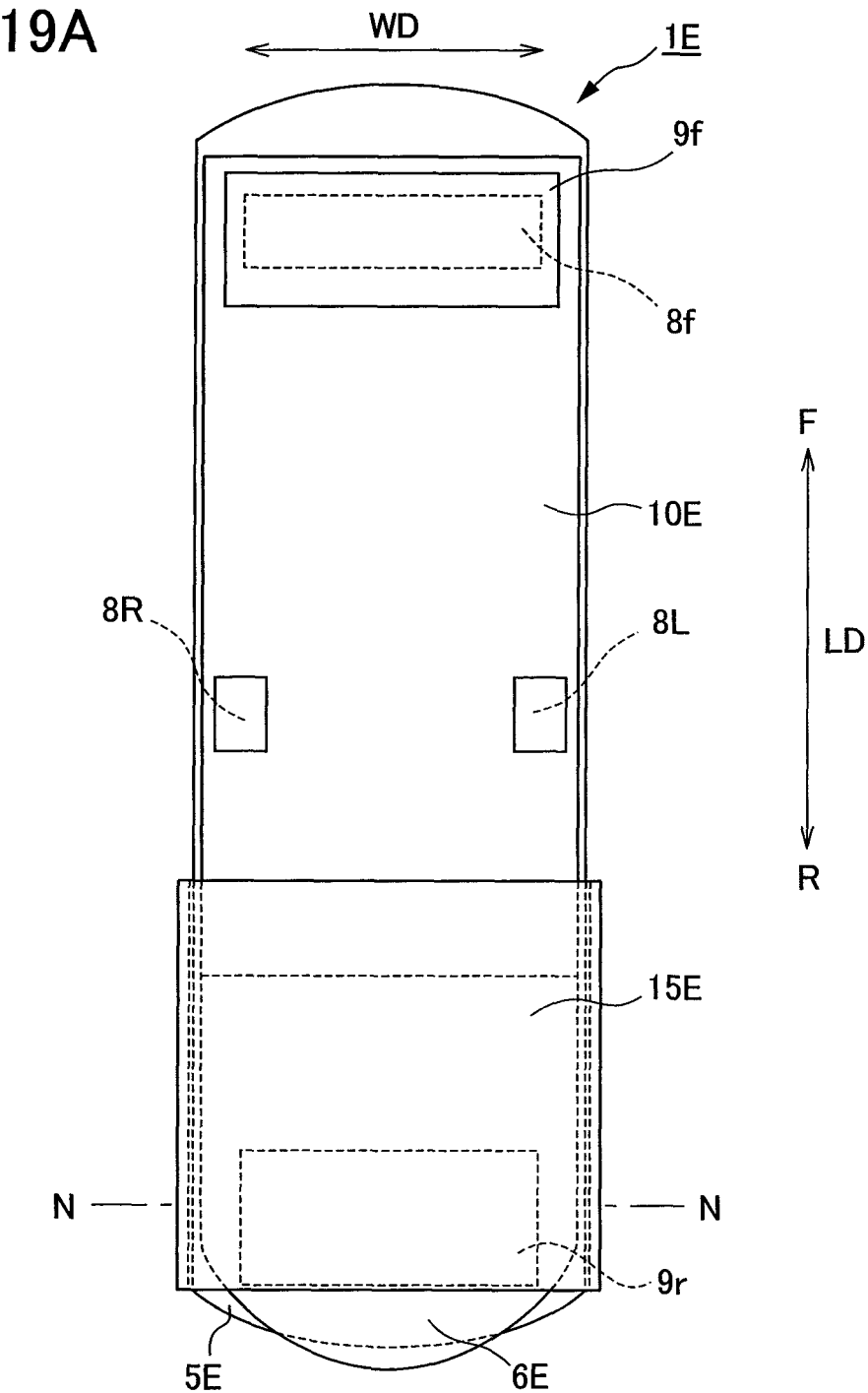
FIG. 19A is a back view according to a sixth embodiment of the present invention.
Figure 19B:
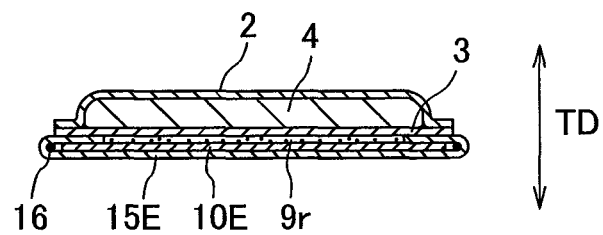
FIG. 19B is a sectional view taken along the line N-N of FIG. 19.
Figure 20:
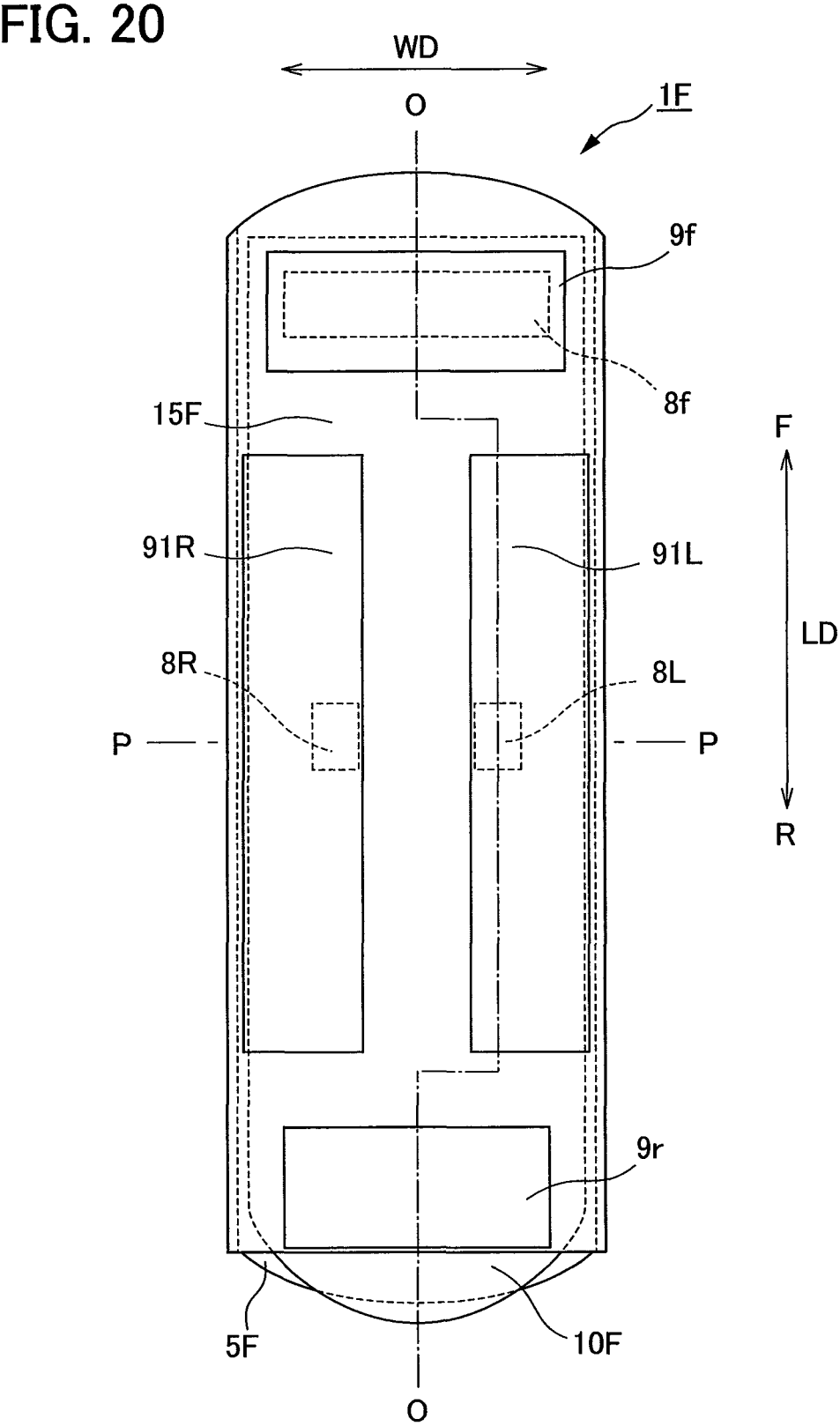
FIG. 20 is a back view of a sanitary napkin according to a seventh embodiment of the present invention.

FIG. 10 is a sectional view taken along the line E-E of FIG. 8. FIG. 11A is a sectional view taken along the line F-F of FIG. 8. FIG. 11B is a sectional view taken along the line G-G of FIG. 8. FIG. 11C is a sectional view taken along the line H-H of FIG. 8. FIG. 12A is a perspective view showing a deformed state of a belt-shaped member according to the second embodiment. FIG. 12B is a perspective view showing an expanded state of the belt-shaped member according to the second embodiment. FIG. 12C is a sectional view taken along the line X-X of FIG. 12B. FIG. 12D is a sectional view taken along the line Y-Y of FIG. 12B. FIG. 13A is a back view of a sanitary napkin according to a third embodiment of the present invention. FIG. 13B is a back view showing an expanded state of the sanitary napkin according to the third embodiment. FIG. 14 is a front view of a sanitary napkin according to a fourth embodiment of the present invention. FIG. 15 is a sectional view taken along the line I-I of FIG. 14. FIG. 16A is a sectional view taken along the line J-J of FIG. 14. FIG. 16B is a sectional view taken along the line K-K of FIG. 14. FIG. 16C is a sectional view taken along the line L-L of FIG. 14. FIG. 16D is a diagram showing another configuration of FIG. 14. FIG. 17 is a back view of a sanitary napkin according to a fifth embodiment of the present invention. FIG. 18A is a sectional view taken along the line M-M of FIG. 17. FIG. 18B is a sectional view taken along the line M-M according to another configuration of FIG. 17. FIG. 19A is a back view according to a sixth embodiment of the present invention. FIG. 19B is a sectional view taken along the line N-N of FIG. 19. FIG. 20 is a back view of a sanitary napkin according to a seventh embodiment of the present invention.

Figure 21A:
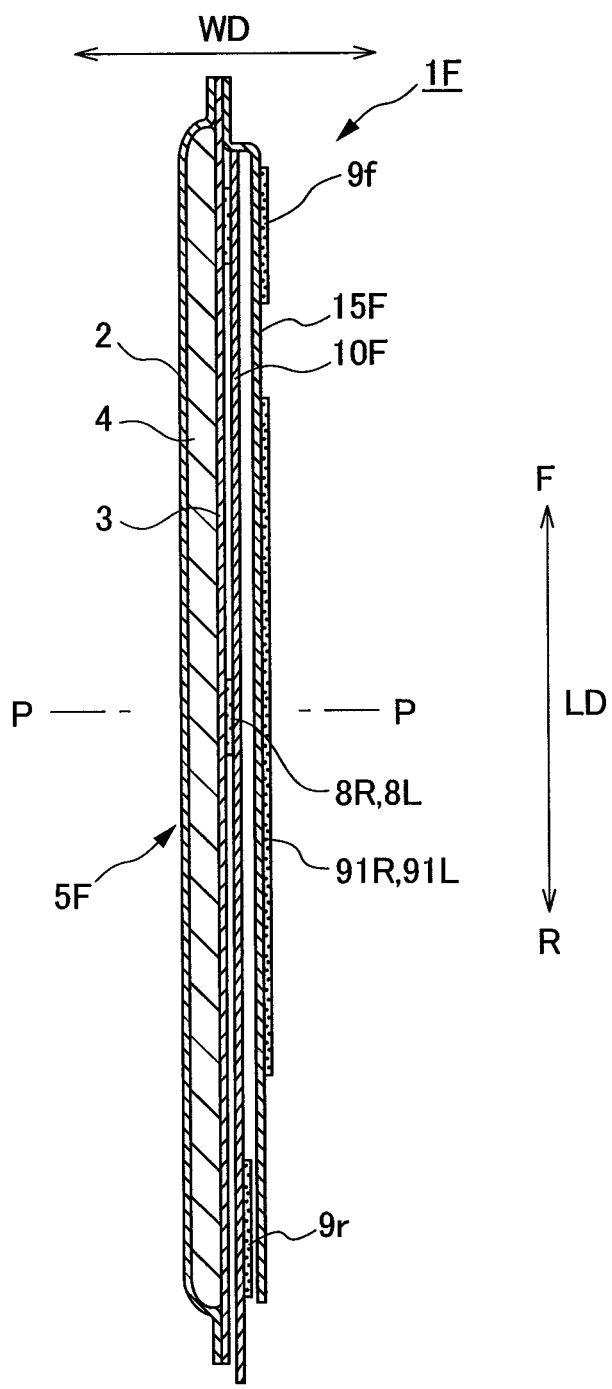
FIG. 21A is a sectional view taken along the line O-O of FIG. 20.
Figure 21B:
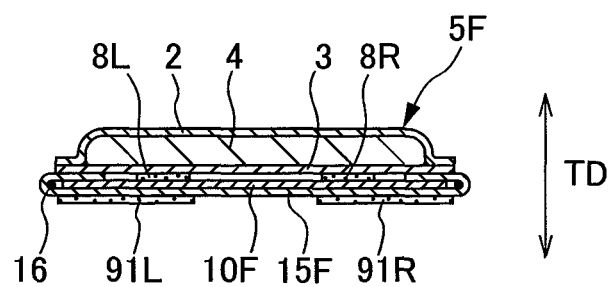
FIG. 21B is a sectional view taken along the line P-P of FIG. 20.
Figure 22A:
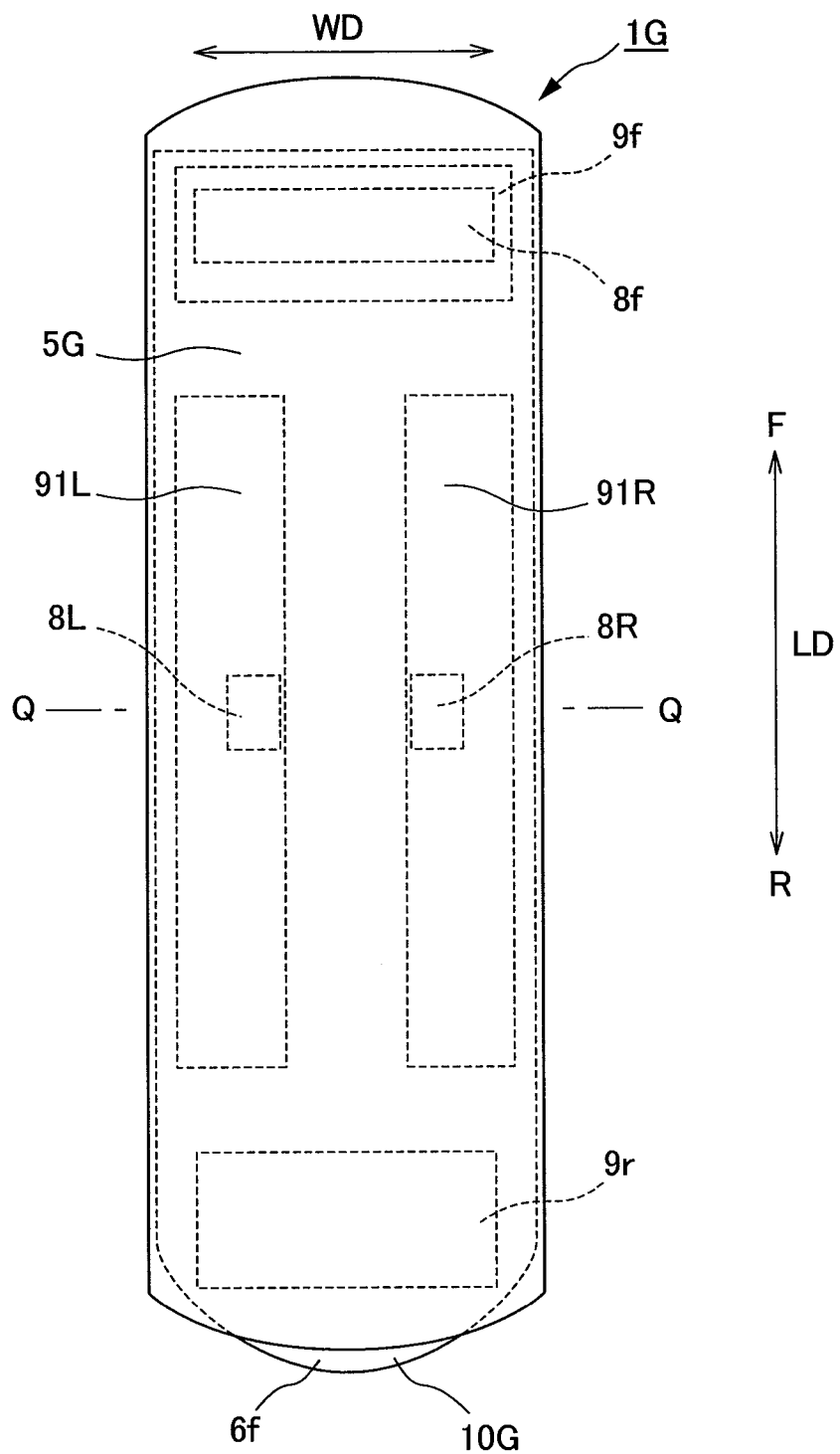
FIG. 22A is a front view of a sanitary napkin according to a eighth embodiment of the present invention.
Figure 22B:
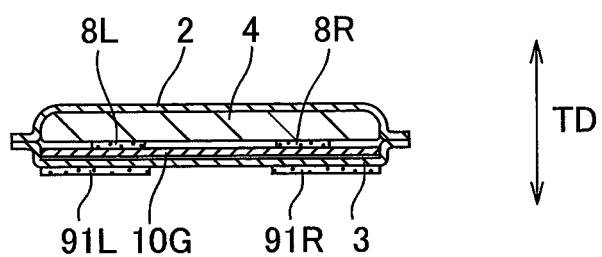
FIG. 22B is a cross-sectional view of FIG. 22A.
Figure 24:
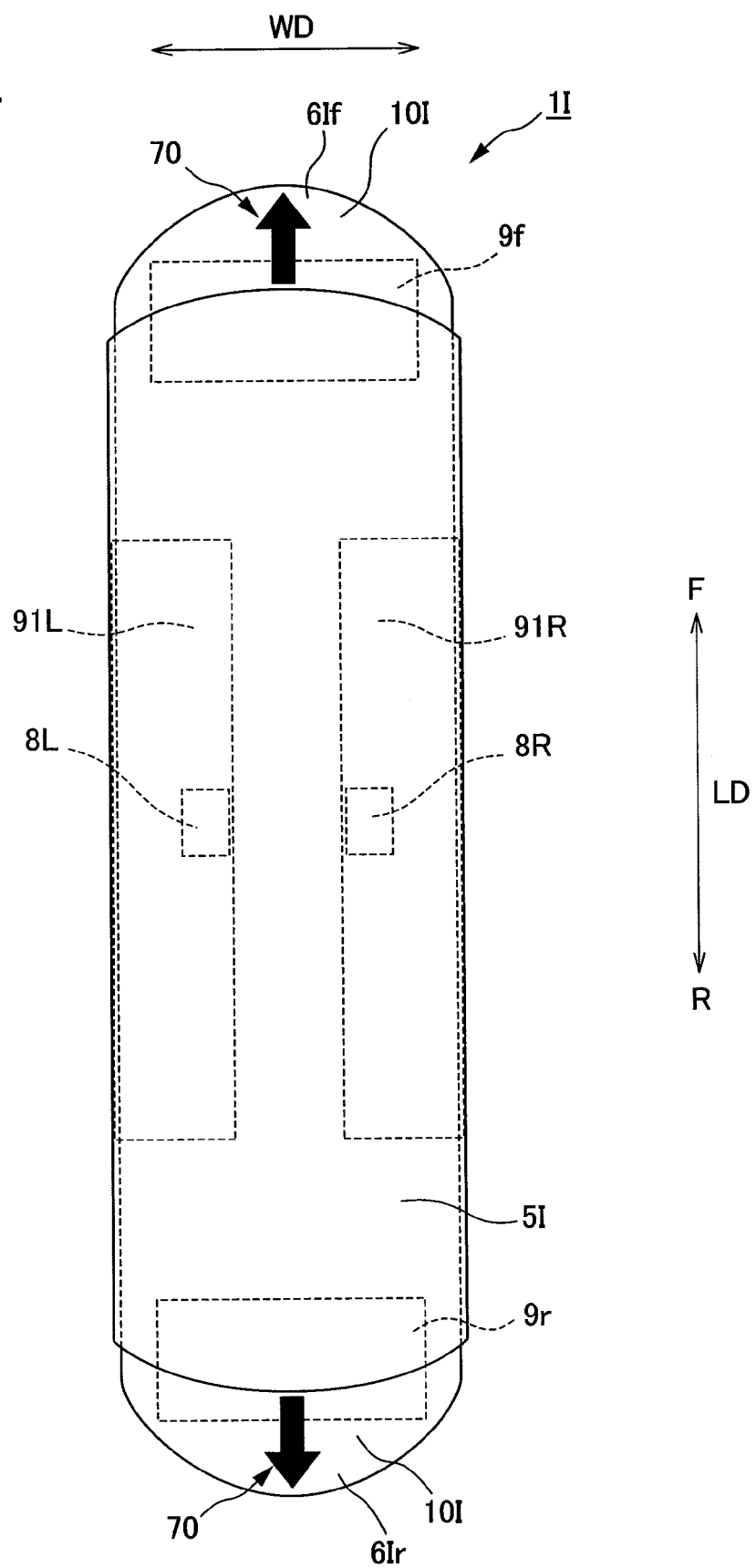
FIG. 24 is a front view of a sanitary napkin according to a tenth embodiment of the present invention.
Figure 25:
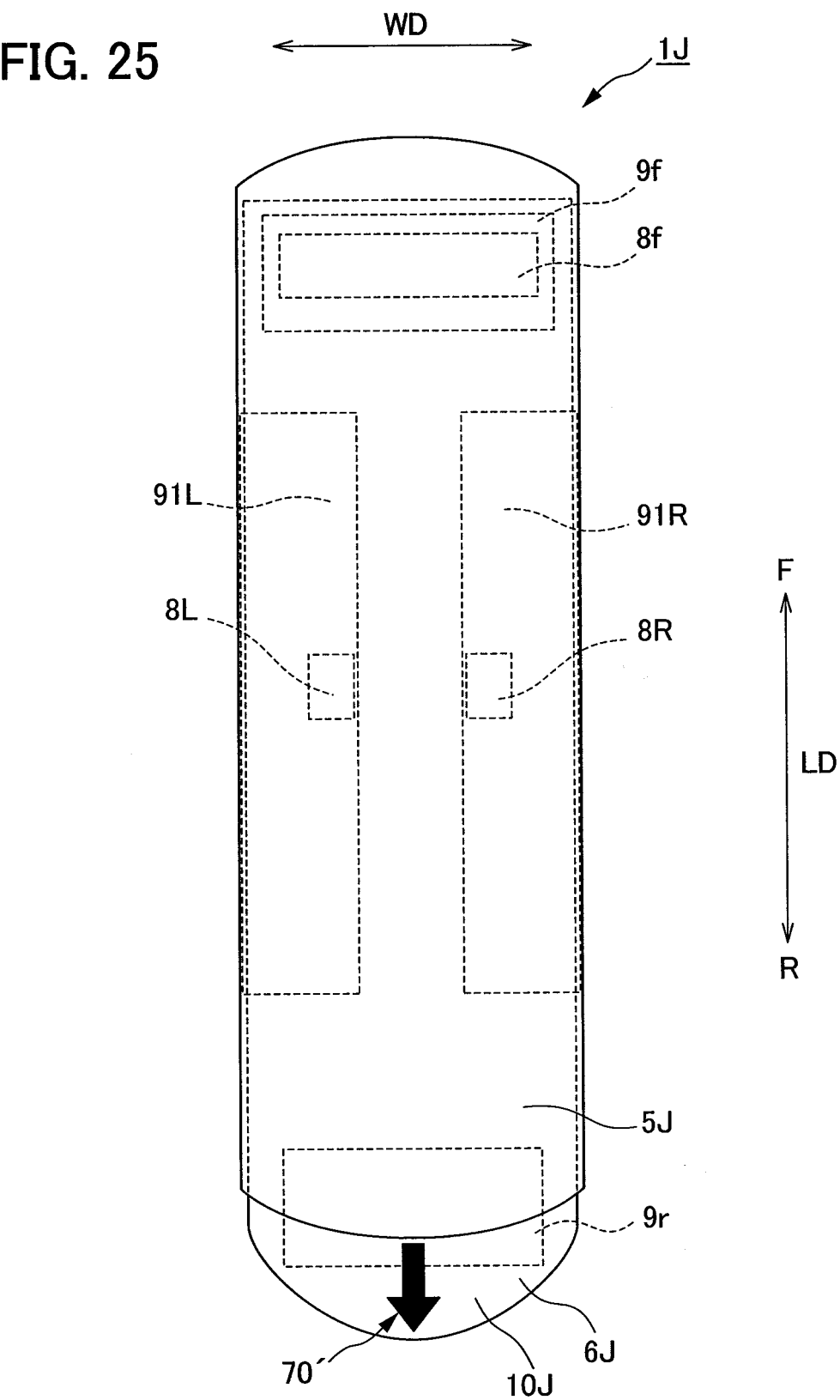
FIG. 25 is a front view of a sanitary napkin according to an eleventh embodiment of the present invention.
Figure 26A:
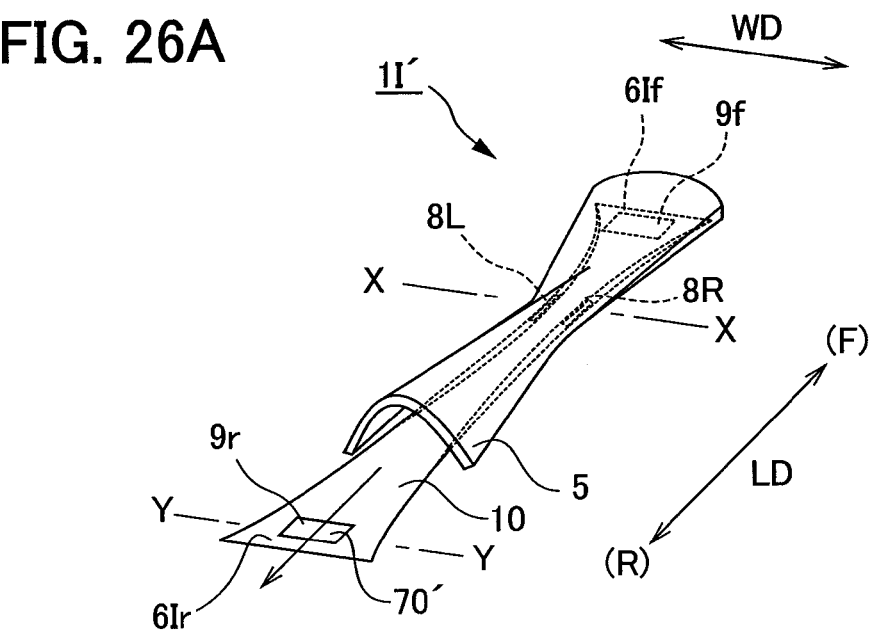
FIG. 26A is a perspective view showing a expanded state of a belt-shaped member according to the eleventh embodiment.
Figure 26B:
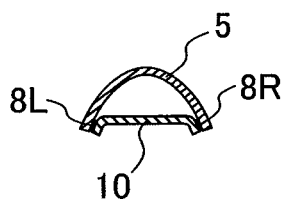
FIG. 26B is a sectional view taken along the line X-X of FIG. 26A.
Figure 26C:
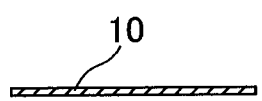
FIG. 26C is a sectional view taken along the line Y-Y of FIG. 26A.
Figure 27B:
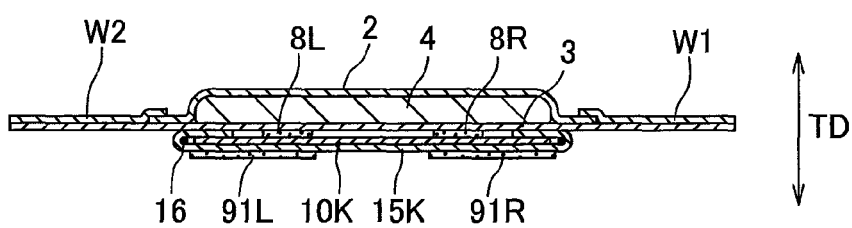
FIG. 27B is a sectional view taken along the line R-R of FIG. 26A.
Figure 28:
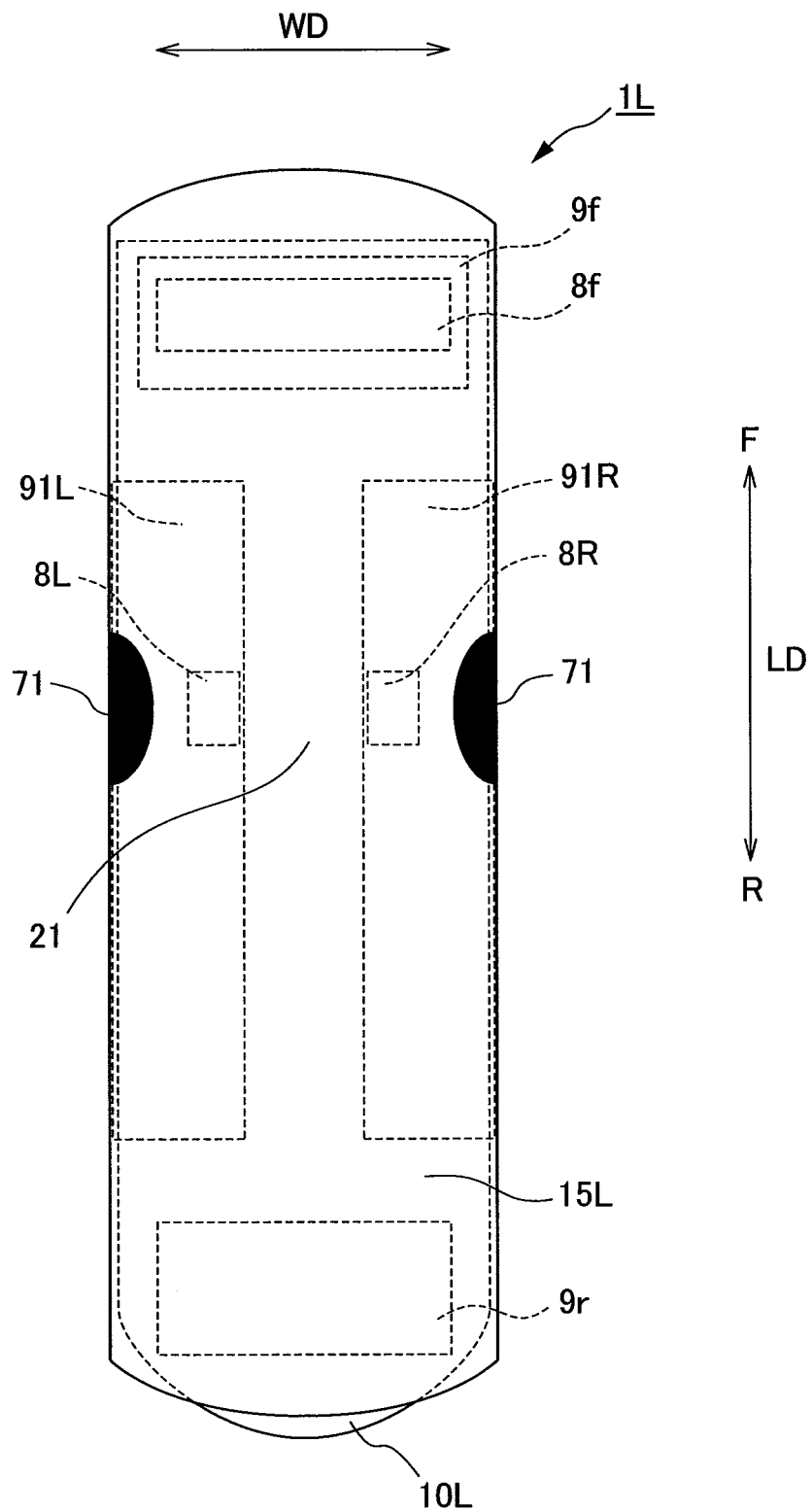
FIG. 28 is a front view of a sanitary napkin according to a thirteenth embodiment of the present invention.
Figure 29:
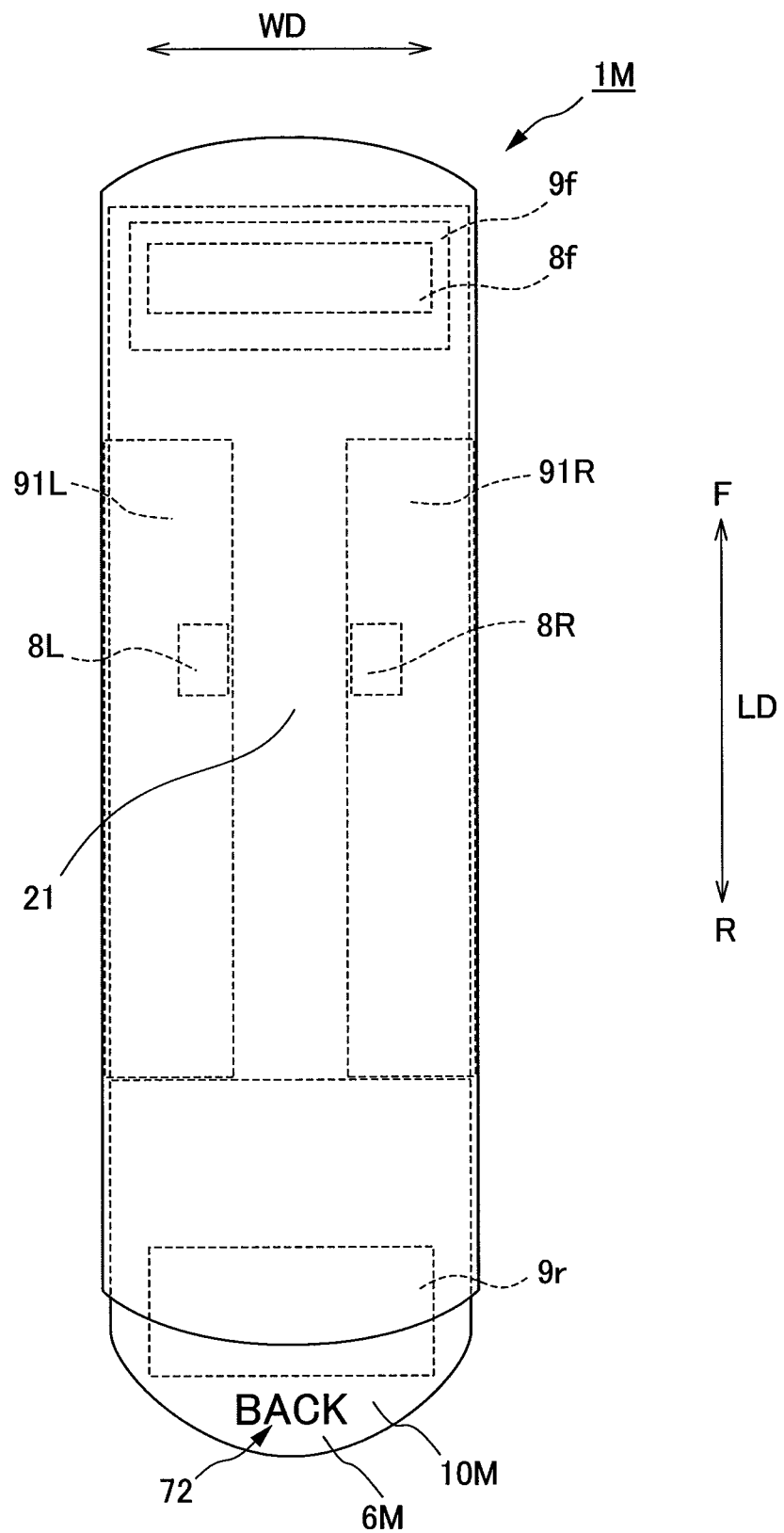
FIG. 29 is a front view of a sanitary napkin according to a fourteenth embodiment of the present invention.

FIG. 21A is a sectional view taken along the line O-O of FIG. 20. FIG. 21B is a sectional view taken along the line P-P of FIG. 20. FIG. 22A is a front view of a sanitary napkin according to a eighth embodiment of the present invention. FIG. 22B is a cross-sectional view of FIG. 22. FIG. 23 is a front view of a sanitary napkin according to a ninth embodiment of the present invention. FIG. 24 is a front view of a sanitary napkin according to a tenth embodiment of the present invention. FIG. 25 is a front view of a sanitary napkin according to an eleventh embodiment of the present invention. FIG. 26A is a perspective view showing an expanded state of a belt-shaped member according to the eleventh embodiment. FIG. 26B is a sectional view taken along the line X-X of FIG. 26A. FIG. 26C is a sectional view taken along the line Y-Y of FIG. 26A. FIG. 27A is a front view of a sanitary napkin according to a twelfth embodiment of the present invention. FIG. 27B is a sectional view taken along the line R-R of FIG. 26A. FIG. 28 is a front view of a sanitary napkin according to a thirteenth embodiment of the present invention. FIG. 29 is a front view of a sanitary napkin according to a fourteenth embodiment of the present invention.

1. First Embodiment 1-1. Overall Configuration

The overall configuration of the absorbent article of the present invention is described based on a sanitary napkin 1 according to a first embodiment of the present invention. The sanitary napkin 1, which is an absorbent article of the first embodiment, is provided with a sanitary napkin main body 5 that is an absorbent article main body, and a belt-shaped member 10. More specifically, as shown in FIGS. 1 to 4C, the sanitary napkin 1 is provided with a sanitary napkin main body 5 having a liquid permeable top sheet portion 2 that constitutes a surface layer and is disposed at the skin contact side of a wearer, a liquid impermeable back sheet portion 3 that constitutes a back layer and is disposed at the skin non-contacting side of the wearer, and a liquid retentive absorbent core portion 4 that constitutes an absorption layer and is interposed between the top sheet portion 2 and the back sheet portion 3; and a belt shaped member disposed on the skin noncontacting side of the back sheet portion 3, and arranged along a longitudinal direction (LD) of the sanitary napkin main body 5, on the other side of the sanitary napkin main body in a thickness direction (TD).

A sanitary napkin main body 5 and the belt-shaped member 10 are joined at a pair of joining portions 8L and 8R provided at a predetermined area in a substantially central portion in the longitudinal direction (LD). More specifically, the joining portions 8L and 8R are each provided at a substantially central portion in a longitudinal direction (LD) of the sanitary napkin 1, and spaced a predetermined distance apart from each other across the center in a width direction (WD). The belt-shaped member 10 is joined with the sanitary napkin main body 5 at the joining portions 8L and 8R, and arranged so as to extend toward a front and back direction in the longitudinal direction (LD) of the sanitary napkin main body 5, with the joining portions 8L and 8R as starting points.

Both end portions in the longitudinal direction (LD) of the belt-shaped member 10 project from the outer edge of both end portions of the sanitary napkin main body 5, and grip portions 6f and 6r are provided at these projected portions, respectively. The skin noncontacting side of the grip portions 6f and 6r is provided with engaging parts 9f and 9r, respectively, which engage with the underwear 50 as a target object. More specifically, the grip portions 6f and 6r are provided slightly toward the central portion side in the longitudinal direction with regard to the both end portions of the belt shaped member 10.

In addition, as another configuration, the sanitary napkin 1 can be further provided with a leak-proof groove portion that can be formed by continuously compressing the top sheet portion 2 and the absorbent core portion 4. Furthermore, a leak-proof wall formed using an elastic member and a leak-proof sheet, a so-called gather, may be arranged along both sides in the width direction (WD) of the sanitary napkin.

Here, the sanitary napkin 1 is folded in three or four with the top sheet portion inside, and individually packed in a package in the form of a packed body, and an opening portion of the package is provided with tape. The inside of the packed body of the sanitary napkin 1 can be processed with a parting agent such as silicon, in order to make tape and the like easily removable from the packed body. In addition, a release paper and the like processed with a parting agent can be provided so as to cover an adhesive portion of the sanitary napkin 1, which is used for fixing the sanitary napkin 1 to underwear or the wearer's body.

1-2. Sanitary Napkin Main Body

As shown in FIGS. 1 and 2, the sanitary napkin main body 5 is formed in a substantially elongated shape. The shape of sanitary napkin main body 5, for example, can be exemplified as a rectangle, an elliptical-shape, and a guitar-shape, as well as a shape including so-called wings W1 and W2 (described later), which prevent dislocation thereof from the underwear 50. Moreover, it should be noted that the present invention may employ any shape suitable for the wearer's body and the shape of the underwear 50. The length of the sanitary napkin main body 5 in the longitudinal direction (LD) is, for example, preferably from 100 to 500 mm, and more preferably from 150 to 350 mm. In addition, the length in the width direction (WD) is, for example, preferably from 30 to 200 mm, and more preferably from 40 to 180 mm.

The sanitary napkin main body 5 has a liquid permeable top sheet portion 2 that constitutes a surface layer and is disposed at the skin contacting side of a wearer, a liquid impermeable back sheet portion 3 that constitutes a back layer and is disposed at the skin noncontacting side of the wearer, and a liquid retainable absorbent core portion 4 that constitutes an absorption layer and is interposed between the top sheet portion 2 and the back sheet portion 3.

A discharged matter such as menstrual blood discharged from the excretion part of the body passes through the surface sheet 2, and is then absorbed by the absorbent body 4. Since the back sheet portion 3 disposed at the non-skin contact surface is liquid impermeable, the excrement can be absorbed and retained by the absorbent core portion 4, without reaching the skin noncontacting side.

The top sheet portion 2 and the absorbent core portion 4 are each adhesively joined with a hot melt adhesive. In addition, the top sheet portion 2 and the back sheet portion 3 are joined by a joining portion (not shown) formed by a hot melt adhesive and hot pressing. In the entirety, surfaces of the sheets are joined with each other with the hot melt adhesive, and edge portions of each sheet are joined by the hot pressing process.

The coating patterns for hot melt adhesion include: spiral coating, controlled seam coating, coater coating, curtain coater coating, summit-gun coating and the like, for example. The weight of the adhesive in the hot melt adhesion is preferably 1 to 30 g/m$^2$, and more preferably 3 to 10 g/m$^2$. In addition, in a case where adhesive is coated in a linear pattern, the diameter thereof is preferably from 30 to 300 μm.

1-3. Belt-Shaped Member

The belt-shaped member 10 is formed in a substantially elongated shape. The length of the belt-shaped member 10 in the width direction (WD) can be exemplified, for example, to be preferably in the range of 30 to 150% of the length of the sanitary napkin main body 5 in the width direction (WD), and more preferably in the range of 60 to 130% thereof. This is because, when the length is less than 30% of the length of the sanitary napkin main body 5 in the width direction (WD), for example, the entirety of the sanitary napkin main body 5 cannot be sufficiently lifted, and thus the entirety of the sanitary napkin main body 5 cannot sufficiently adhere to the wearer's body. Alternatively, in a case where the length is greater than 150% thereof, the area to be in contact with the thighs of the wearer is excessive, and skin irritation or the like may occur by frictional contact therewith.

In addition, the length of the belt-shaped member 10 in the longitudinal direction (LD) can be exemplified, for example, to be preferably in the range of 30 to 300% of the length of the sanitary napkin main body 5 in the longitudinal direction (LD), and more preferably in the range of 70 to 150% thereof. This is because, when the length of the belt-shaped member 10 in the longitudinal direction (LD) is below 30% of the length of the sanitary napkin main body 5 in the longitudinal direction (LD), the sanitary napkin main body 5 cannot sufficiently contact the human body, even if the belt-shaped member 10 is expanded. Alternatively, when the length of the belt-shaped member 10 in the longitudinal direction (LD) is greater than 150% thereof, the area to be in contact with the thighs of the wearer is excessive, and skin irritation or the like may occur by frictional contact therewith. In addition, for example, the belt-shaped member 10 in the expanded state might not be attached to the underwear 50, and might not adhere to the excretory part.

In addition, the expandable range of the belt-shaped member 10 is preferably can be exemplified, for example, to be preferably in the range of 105 to 300%, and more preferably in the range of 110 to 180% thereof, with 100% being the non-expanded state. This is because, when the expanded state is less than 105%, the stress for pressing the sanitary napkin main body 5 against the wearer's body becomes weak, it is difficult to establish the structure for lifting the sanitary napkin main body 5. In addition, this is because when the expanded state is greater than 300%, an excessive push-up force to the human body than necessary is developed, and the wearer might feel discomfort. Furthermore, the stress of the belt-shaped member 10, in the expanded state of 105 to 300% in extension rate, is preferably, for example, in the range of from 5 to 500 cN/25 mm, and more preferably from 20 to 100 cN/25 mm.

A sheet member formed to be expandable in the longitudinal direction (LD) and to be deformable in the width direction (WD) is used for the belt-shaped member 10. It should be noted that the belt-shaped member 10 can be of any material that is to be in a so-called neck-in state where the width narrows in a width direction (WD) (hereinafter simply referred to as "neck-in"), in a case of being expanded in a longitudinal direction (LD). A range for the neck-in is, for example, 20 to 95% of a non-expanded state being joined with the sanitary napkin main body 5. More preferably, a range of 50 to 80% can be exemplified. For example, a fibrous sheet using thermoplastic elastomer resin may be used for the belt-shaped member 10. More specifically, a fibrous sheet including: a non-woven fabric obtained by blending urethane fiber and synthetic fiber; a non-woven fabric including a layer obtained by forming elastomer resin by melt blowing; and a film sheet can be exemplified. Especially, in a case where a stretchable fiber aggregate is used, the belt-shaped member can be neck-in with a light load, since a fiber orientation thereof is subjectively in the width direction (WD) and a fiber form thereof can be easily deformed when being expanded in the longitudinal direction (LD).

The belt-shaped member 10 has a grip portion 6 in each of the front region (F) and the rear region (R) in the longitudinal direction (LD). The grip portion 6 is disposed in each end in the longitudinal direction (LD) of the belt-shaped member 10, so as to project from of the outer edge of the sanitary napkin main body 5. This allows, for example, the wearer to easily recognize the grip portion 6, thereby preventing the wearer from inappropriately wearing the sanitary napkin. The grip portion 6 may be projected from the edge, to such a degree that the wearer can pinch it by fingers and the like. Furthermore, the grip portion 6 being an inexpandable region is preferable.

1-4. Position to Connect Sanitary Napkin Main Body and Belt-Shaped Member

The sanitary napkin main body 5 and the belt-shaped member 10 are joined with each other by joining portions 8R and 8L, provided in each side portion of a liquid permeable region 21 in a substantially central portion of the sanitary napkin 1, spaced a predetermined distance apart from each other across the center in the width direction (WD). The substantially central portion that is the liquid permeable region 21 in the longitudinal direction (LD), due to being the location where neck-in is the most in a case where the belt-shaped member 10 is stretched, the sanitary napkin main body 5 and the belt-shaped member 10 are preferably joined in the substantially central portion of the sanitary napkin 1.

For example, the distance between each of the joining portions 8R and 8L in the width direction (WD) can be exemplified as being in the range of 5 to 200 mm. More preferably, the range of 30 to 80 mm can be exemplified. This is because, when the distance between joining portions 8R and 8L in the width direction (WD) is less than 5 mm, the sanitary napkin main body 5 cannot be sufficiently lifted up, even if the belt-shaped member 10 is neck-in. Alternatively, when the distance between joining portions 8R and 8L in the width direction (WD) is greater than 200 mm, the sanitary napkin main body 5 is excessively lifted up and the wearer may feel a foreign-body sensation.

In addition, as the distance between each of the joining portions 8R and 8L in the width direction (WD) relative to a length in the width direction (WD) of the sanitary napkin main body 5, a range of 5 to 95% thereof can be exemplified. More preferably, the range of 30 to 80% can be exemplified. This is because, when the distance between each of the joining portions 8R and 8L in the width direction (WD) in relation to a length in the width direction (WD) of the sanitary napkin main body 5 is less than 5% thereof, the sanitary napkin main body 5 cannot be sufficiently lifted up, even if the belt-shaped member 10 is neck-in. Alternatively, when the distance between each of the joining portions 8R and 8L in the width direction (WD) in relation to a length in the width direction (WD) of the sanitary napkin main body 5 is greater than 95% thereof, the sanitary napkin main body 5 is excessively lifted up and the wearer may feel a foreign-body sensation.

A position to join the belt-shaped member 10 with the sanitary napkin main body 5 in the longitudinal direction (LD) must be chosen so as not to eliminate the stretchability of the belt-shaped member 10. For example, in a case where the belt-shaped member 10 is joined with the sanitary napkin main body 5 in the two portions spaced apart from each other in the longitudinal direction (LD), the stretchability of the belt-shaped member 10 is eliminated in the region between the portions since the sanitary napkin main body 5 is not stretchable. In addition, also in a case where the joining portions 8R and 8L are disposed lengthwise in the longitudinal direction (LD), the stretchability of the belt-shaped member 10 is eliminated in the region therebetween since the sanitary napkin main body 5 is not stretched. Therefore, the joining position, for example, is preferred to be disposed at a location where the stretchability of the belt-shaped member is not of vital importance. For example, joining is preferable in the vicinity of the wearer's excretory part, and more specifically the wearer's vaginal opening. The sanitary napkin main body 5 is not largely deformed and remains substantially flat in the vicinity of the excretory part in the longitudinal direction, and begins to curve along the wearer's body from the front end and the rear end of the excretory part. Thus, in the vicinity of the excretory part, the sanitary napkin main body 5 can be lifted up by the belt-shaped member 10 in the front and the rear thereof expanding, even without the direct stretchability of the belt-shaped member 10. This is because a force is thus generated that makes the sanitary napkin main body 5 adhere to the wearer's body.

For example, the joining range of the sanitary napkin main body 5 and the belt-shaped member 10, in other words a length of the joining portion in the longitudinal direction (LD), is preferably that which includes a position covering the wearer's excretory part. More specifically, that including the vicinity of the vaginal opening is preferred. More preferably, the region across the liquid permeable region 21 in the substantially central portion of the sanitary napkin main body 5 being in contact with the vaginal opening can be exemplified to be preferably within the range of less than 20 mm, and more preferably within the range of 1 to 10 mm, in each of the front (F) and the rear (R) regions. When either of the front region (F) or the rear region (R) is greater than 20 mm, the portion of the belt-shaped member 10 without the stretchability is too large, and the sanitary napkin main body 5 may be easily detached from the excretory part due to a change in wearer's posture.

In addition, in the width direction (WD), a range of 10 to 100% can be exemplified in the width (WD) of the sanitary napkin main body 5. Preferably, that in the range of 60 to 100% can be exemplified. In the width direction (WD), either that fixed continuously or fixed intermittently may be used. A hot melt adhesive, embossing finish, sonic process and the like can be exemplified as the joining material.

1-5. Position to Engage Belt-Shaped Member with Underwear

The belt-shaped member 10 has the engaging portions 9f and 9r to be engaged with the underwear 50 or the like, in each of both ends in the longitudinal direction (LD), at a nonskin-contacting side of the belt shaped member 10. The engaging portion 9f is engaged with the underwear 50 or the like in the front region (F), and the engaging portion 9r is engaged the underwear 50 in the rear region (R). The sanitary napkin main body 5 is not largely deformed and remains substantially flat in the vicinity of the excretory part in the longitudinal direction, and begins to curve along the wearer's body from the front end and the rear end of the excretory part. Thus, by engaging the engaging portions 9f and 9r with the underwear 50 or the like in the front region (F) and the rear region (R), the extension range of the belt-shaped member 10 becomes greater and the sanitary napkin main body 5 is lifted along the curve of the wearer's body. Consequently, the stress from the belt-shaped member 10 is easily transferred to the liquid permeable region 21 disposed in the vicinity of the excretory part. In addition, the engaging portions 9f and 9r are preferably provided in both end portions of the belt-shaped member 10, slightly toward the central portion side in the longitudinal direction (LD). This is to prevent the engaging material from sticking to wearer's fingers and the like when the wearer pinches the grip portions 6f and 6r.

A hot melt adhesive, hook material, binder, and the like, for example, can be exemplified as the engaging material used for the engaging portions 9f and 9r. The engaging material used for the engaging part 9r provided in the rear region (R) may be an engaging material for engaging with the underwear 50 or an engaging material for engaging with the wearer's body. In other words, the engaging portions may be engaged either with the underwear 50 or the like, or may be adhered to the wearer's body.

Furthermore, in order to prevent the belt-shaped member 10 from slipping from the underwear or the like during wearing, in a case where the belt-shaped member 10 has stretchability, the engaging force of the engaging material is required to be larger than the contractive force of the belt-shaped member 10. Accordingly, the shear stress, in other words the engaging force, is preferably set to be larger than the contractive force which has the range of 5 to 500 cN/25 mm.

1-6. Mode of Usage

Modes of usage of the sanitary napkin 1 in the first preferred embodiment of the present invention are described with reference to FIGS. 6 and 7. More specifically, the sanitary napkin 1 in the first preferred embodiment has a first mode of usage and a second mode of usage.

The first and the second modes of usage, regarding the method of applying the sanitary napkin 1 to the underwear 50 (target object) in the wearing process of the sanitary napkin 1, are described as an example of mode of usage thereof.

In the first mode of usage, the sanitary napkin 1 is first arranged at a predetermined position of the underwear 50. Thereafter, a wearer holds the grip portions 6*f* and 6*r* provided in the both ends of the belt-shaped member 10, and pulls each thereof toward the front region (F) and the rear region (R), respectively. The belt-shaped member 10 is thus expanded. Here, in a case where the sanitary napkin 1 is provided with the cover member 15 described later, the engaging portions 9*f* and 9*r* appear on the skin noncontacting side of the belt-shaped member 10, when the wearer pulls the belt-shaped member 10. After expanding the belt-shaped member 10 to a predetermined degree, the wearer engages the engaging portions 9*f* and 9*r* provided in both ends of the skin noncontacting side thereof to a predetermined position on the underwear 50 being a target object. More specifically, the engaging material of the engaging portions 9*f* and 9*r* is adhered to the underwear 50. At this time, the engaging material can be exposed by removing a release paper (not shown) on the skin noncontacting side of the engaging portions 9*f* and 9*r*. It should be noted that the term "predetermined position on the underwear 50" includes, for example, an expected position where the liquid permeable region 21 of the sanitary napkin 1 can be brought into contact with the wearer's excretory part. Moreover, the belt-shaped member 10 is preferably expanded as much as possible to be adhered to the underwear 50.

On the completion of the attachment of the sanitary napkin 1, the underwear 50 is worn in this state so that the belt-shaped member 10 and the sanitary napkin 5 can be deformed in a gentle curve, and stress can be transferred from the belt-shaped member 10 to the sanitary napkin main body 5 toward the wearer's body. At this time, the belt-shaped member 10 lifts and pushes the sanitary napkin main body 5 against the wearer's body. As a result, the wearer's excretory part and the groove in the vicinity thereof can be in close contact with the sanitary napkin 1 (refer to FIG. 7).

As the second manner of use, the sanitary napkin 1 is arranged at the same position as in the first manner of use. In this state, the underwear 50 is put on. Thereafter, a wearer holds the grip portions 6*f* and 6*r* provided on the belt-shaped member 10 by inserting hands between the underwear 50 and the wearer's body in each of the front region (F) and the rear region (R), and pulls each thereof toward the front region (F) and the rear region (R), respectively, along the curve of the body. Here, for example, in a case where the sanitary napkin 1 is provided with the cover member 15 (described later), the engaging portions 9*f* and 9*r* provided on the skin noncontacting side of the belt-shaped member 10 appear when the wearer pulls the grip portions 6*f* and 6*r*. In addition, fixing is to a predetermined position on the underwear 50.

It should be noted that, for example, if the engaging portion 9*r* is provided with a removable sheet, the removable sheet may be removed in advance or removed after, or before pulling in the longitudinal direction (LD).

At this time, as shown in FIG. 7, the underwear 50 is now lifted toward the wearer's body together with the sanitary napkin 1, and therefore, by engaging the grip portions 6*f* and 6*r* on both ends of the belt-shaped member 10 with the underwear 50 by pulling, the position of the sanitary napkin 1 can be adjusted so that the sanitary napkin 1 better adheres to the groove in the vicinity of the wearer's excretory part.

Thus, since the wearer fixes the belt-shaped member 10 to the underwear 50 by pinching the grip portions 6*f* and 6*r* and pulling the belt-shaped member 10 toward the front region (F) and the rear region (R), tension in the longitudinal direction can be exerted on the belt-shaped member 10. Thereafter, by bringing the belt-shaped member 10 toward the wearer's body, the belt-shaped member 10 and the sanitary napkin main body 5 can be deformed in a gentle curve, and stress can be transferred from the belt-shaped member 10 to the sanitary napkin main body 5 toward the wearer's body. At this time, the belt-shaped member 10 lifts and pushes the sanitary napkin main body against the wearer's body. As a result, the wearer's excretory part and the groove in the vicinity thereof can be in close contact with the sanitary napkin 1 (refer to FIG. 7).

In addition, the sanitary napkin main body 5 is deformed into a convex shape by pulling the belt-shaped member 10. More specifically, as shown in FIG. 6B, since the belt-shaped member 10 is in a neck-in state when being pulled, in other words, the substantially central portion in the longitudinal direction (LD) of the belt-shaped member 10 becomes narrower than both end portions thereof (see FIGS. 6C and 6D), each of the joining portions 8L and 8R, for joining the belt-shaped member 10 with the sanitary napkin main body 5, approach each other in the width direction (WD). Thus, as each of the joining portions 8L and 8R approach each other in the width direction (WD), the sanitary napkin main body 5 joined with the belt-shaped member 10 is deformed so as to project to one side (see FIG. 6C). Therefore, by adjusting the degree of expansion of the belt-shaped member 10, the degree of deformation of the sanitary napkin main body 5 can be adjusted.

It should be noted that, the mode of usage in the present embodiment, as an alternative mode of usage in the present embodiment, can use a configuration in which the belt-shaped member 10 is not used. In this case, the belt-shaped member 10 can be used after the underwear 50 is put on.

2. Other Embodiments

Referring to FIGS. 8 to 29, the second to fourteenth embodiments of the present invention are described hereinafter. The second embodiment shows another embodiment relating to the direction of stretch of the belt-shaped member 10. The third embodiment shows another embodiment of the belt-shaped member 10. The fourth to the sixth embodiments show other preferred embodiments with the cover member 15 provided. The seventh embodiment shows another preferred embodiment with respect to engaging portions 91R and 91L of the belt-shaped member. The eighth embodiment shows another embodiment regarding the position where the belt-shaped member 10 is provided. The ninth preferred embodiment shows another embodiment where the belt-shaped member 10 does not have the engaging portion 9*r*. The tenth and eleventh preferred embodiments show other preferred embodiments regarding a guide element of the belt-shaped member 10. The twelfth to the fourteenth preferred embodiments show other preferred embodiments regarding a suggestion for the liquid permeable region 21 of the sanitary napkin main body 5.

In the following description, the same reference numerals have been retained for similar parts that are identical to that described in the first embodiment, with the description thereof omitted.

2.1. Second Embodiment

A sanitary napkin 1A of the second embodiment of the present invention is described with reference to FIGS. 8 to 12D. As shown in FIGS. 8 to 12D, the sanitary napkin 1A of the second embodiment is different from the first preferred embodiment in an expanding direction of the belt-shaped member 10A. More specifically, as shown in FIGS. 8 to 11C, in the sanitary napkin 1A, the belt-shaped member 10A is joined with the sanitary napkin main body 5A also in the front region (F) that is a first end side. In addition, the sanitary napkin 1A is formed to be expandable in a second end side, which is at an opposing side of a first end side, and a part of the belt-shaped member 10A is projected from an outer edge in the second end side of the sanitary napkin main body 5A. In other words, only the second end side is formed to be expandable.

More specifically, the sanitary napkin main body 5A and the belt-shaped member 10A are joined with each other at joining portions 8f, 8R, and 8L. The joining portion 8f for joining the belt-shaped member 10A with the sanitary napkin main body 5A is preferably in the front region (F) away from the wearer's vaginal opening when the sanitary napkin 1A is put on. For example, the joining portion 8f is preferably located at a swelling part in the vicinity of the wearer's excretory part. More specifically, a position corresponding to the pubis in the vicinity of the vaginal opening is preferable. Since the position corresponding to the pubis is harder than the surroundings and slightly swelled, for example, the pressure from the underwear 50 can be increased, thereby suppressing dislocation of the sanitary napkin main body 5 from the wearer's body. Thus, even if the belt-shaped member 10A is pulled and expanded at the time of attachment, for example, the sanitary napkin main body 5A does not bend due to the stress induced by expanding. As a result, dislocation of the sanitary napkin main body 5 can be suppressed at the time of attachment and during wearing thereof.

The belt-shaped member 10A has the engaging portions 9f and 9r to be engaged with the underwear 50 or the like, in each of both end portion sides in the longitudinal direction (LD). The engaging portion 9f is engaged with the underwear 50 or the like in the front region (F), and the engaging portion 9r is engaged therewith in the rear region (R). Here, providing the engaging portion 9f, for example, at a position opposite to the joining portion 8f, where the sanitary napkin main body 5A and the belt-shaped member 10A are joined with each other is preferred. This is because the joining portion 8f for joining the sanitary napkin main body 5A and the belt-shaped member 10A is one of the origins of the belt-shaped member 10A to the second end side, and also the point where the tension of the belt-shaped member 10A to the sanitary napkin main body 5A is maximized, thus preventing the sanitary napkin main body 5A from dislocating from the underwear 50.

The engaging portion 9r being located slightly ahead of the rearmost end in the rear end portion of the belt-shaped member 10A is preferred. This is because, since the human body is often significantly curved from the vaginal opening to the rear, the expansion range of the belt-shaped member 10A in the rear is widened. In addition, the expansion of the belt-shaped member 10A along the curvature of the human body facilitates the transfer of the stress on the belt-shaped member 10A to the sanitary napkin main body 5A located in the vicinity of the excretory part. Furthermore, by disposing the engaging portion 9r slightly ahead of the rearmost end in the rear end portion of the belt-shaped member 10A, it is also possible to prevent the engaging material from being adhered to fingers or the like when the wearer grips the grip portion 6A.

The sanitary napkin 1A of the second embodiment has a first mode of usage and a second mode of usage.

The first and the second modes of usage, regarding the method of applying the sanitary napkin 1A to the underwear 50 (target object) in the wearing process of the sanitary napkin 1A, are described as an example mode of usage of the sanitary napkin 1A with regards to the present embodiment.

In the first mode of usage, the sanitary napkin 1A is arranged at a predetermined position of the underwear 50, and the engaging portion 9f provided in the first end of the belt-shaped member 10A is engaged with a portion of the underwear 50 corresponding to the front region (F). Thereafter, the grip portion 6A is held and pulled toward the rear region (R). The belt-shaped member 10A is thus expanded. Here, in a case where the sanitary napkin 1A is provided with the cover member 15 (described later), by pulling the belt-shaped member 10A, the engaging portion 9r appears on the skin noncontacting side of the belt-shaped member 10A. After expanding the belt-shaped member 10A to a predetermined degree, the engaging portion 9r provided on the skin noncontacting side of the belt-shaped member 10A is engaged at a predetermined position on the underwear 50 being a target object. More specifically, the engaging material of the engaging portion 9r is adhered to the underwear 50. At this time, the engaging material can be exposed by removing a release paper (not shown) on the skin noncontacting side of the engaging portion 9r. It should be noted that the term "predetermined position on the underwear 50" includes, for example, an expected position where the liquid permeable region 21 of the sanitary napkin 1A can be brought into contact with the wearer's excretory part.

Upon the completion of the attachment of the sanitary napkin 1A, the underwear 50 is worn in this state so that the belt-shaped member 10 and the sanitary napkin 5 can be deformed in a gentle curve, and stress can be transferred from the belt-shaped member 10A to the sanitary napkin main body 5A toward the wearer's body. The belt-shaped member 10A lifts and pushes the sanitary napkin main body 5A against the wearer's body. As a result, the wearer's excretory part and the groove in the vicinity thereof can be in close contact with the sanitary napkin 1A.

In the second mode of usage, the sanitary napkin 1A is arranged at the same position as in the first manner of use, and the engaging portion 9f provided in the first end of the belt-shaped member 10A is engaged with a portion of the underwear 50 corresponding to the front region (F). In this state, the underwear 50 is put on. Thereafter, inserting hands between the underwear 50 and the wearer's body in the rear region (R), the grip portion 6A provided on the belt-shaped member 10A is held, and pulled toward the rear region (R) along the curvature of the body. Here, in a case where the sanitary napkin 1 is provided with the cover member 15 (described later), the engaging portions 9r provided on the skin noncontacting side of the belt-shaped member 10 appears when the wearer pulls the grip portions 6A. Moreover, the sanitary napkin 1 is fixed to a predetermined position on the underwear 50.

It should be noted that, if the engaging portion 9r is provided with a removable sheet, for example, the removable sheet may be removed in advance or removed after, or before pulling in the longitudinal direction (LD).

At this time, since the underwear 50 is lifted toward the wearer's body together with the sanitary napkin 1A, by engaging the grip portion 6A of the belt-shaped member 10A with the underwear 50 by pulling, the position of the sanitary napkin 1A can be adjusted so that the sanitary napkin 1A better adheres to the groove in the vicinity of the wearer's excretory part. In addition, since a degree of projection in the thickness direction (TD) of the sanitary napkin main body 5A can be adjusted in accordance with the expansion length of the belt-shaped member 10A, adjustment may be made here.

By thus bringing the belt-shaped member 10A toward the wearer's body, a stress in the longitudinal direction (LD) is generated on the belt-shaped member 10A, and thus the belt-shaped member 10A and the sanitary napkin main body 5A can be deformed in a gentle curve. The belt-shaped member 10A transfers the stress from the belt-shaped member 10A to the sanitary napkin main body 5A toward the wearer's body. The belt-shaped member 10A lifts and pushes the sanitary napkin main body against the wearer's body. As a result, the wearer's excretory part and the groove in the vicinity thereof can be in close contact with the sanitary napkin 1A.

Here, as shown in FIGS. 12A to 12D, the sanitary napkin main body 5 is deformed into a convex shape by pulling the belt-shaped member 10A. More specifically, as shown in FIG. 12B, the belt-shaped member 10A is in a neck-in state when being pulled, in other words, since a predetermined portion in the longitudinal direction (LD) of the belt-shaped member 10A becomes narrower than an end portion thereof (see FIGS. 12C and 12D), the joining portions 8L and 8R, for joining the belt-shaped member 10A with the sanitary napkin main body 5A, approach each other in the width direction (WD). As the joining portions 8L and 8R approach each other in the width direction (WD), the sanitary napkin main body 5A joined with the belt-shaped member 10A is deformed so as to project to one side (see FIG. 12C). Therefore, by adjusting the degree of expansion of the belt-shaped member 10A, the degree of deformation of the sanitary napkin main body 5A can be adjusted.

2.2. Third Embodiment

A sanitary napkin 1B of the third embodiment of the present invention is described with reference to FIGS. 13A and 13B. As shown in FIGS. 13A and 13B, the sanitary napkin 1B of the third embodiment of the present invention is different from the first embodiment in a joined state of the sanitary napkin main body 5B and the belt-shaped member 10B.

More specifically, as shown in FIG. 13A, the sanitary napkin 1B of the third embodiment has a connecting belt 80 for connecting the joining portions 8R and 8L, which are for joining the sanitary napkin main body 5B with the belt-shaped member 10B. A first end side of the belt-shaped member 10B is joined with the connecting belt 80. Moreover, by pulling a second end side, which is the opposing side of the first end side of the belt-shaped member 10B in the longitudinal direction (LD), the connecting belt 80 is deformed, and the joining portions 8R and 8L, for joining the connecting belt 80 with the sanitary napkin main body 5B, approach each other in the width direction (WD) and the length in the width direction (WD) of the sanitary napkin main body 5B is thus decreased. The sanitary napkin main body 5B is thus deformed to project to the skin contacting side (see FIG. 13B). It should be noted that the connecting belt 80 and the belt-shaped member 10B may be formed either of the same member or of different members. In other words, the connecting belt 80 and the belt-shaped member 10B may be integrally formed.

2-3. Fourth to Seventh Preferred Embodiments

Sanitary napkins 1C, 1D and 1E of the fourth to the sixth embodiments are described with reference to FIGS. 14 to 19B. As shown in FIGS. 14 to 19B, the sanitary napkins 1C, 1D and 1E of the fourth to the sixth embodiments are different from the first embodiment in having a cover member 15.

More specifically, as shown in FIGS. 14 to 16D, the sanitary napkin 1C of the fourth embodiment has the cover member 15C covering at least a part of the belt-shaped member 10 on the skin noncontacting side of a sanitary napkin main body 5C. Even more specifically, the cover member 15C covers at least a part in the longitudinal direction (LD) and the entirety in the width direction (WD) of the belt-shaped member 10C. The belt-shaped member 10C is disposed to be slidable between the sanitary napkin main body 5C and the cover member 15C, from the joining portions 8f, 8R, and 8L as a starting point.

In the fourth embodiment, the cover member 15C and the sanitary napkin main body 5C are joined with each other on both side portions of the sanitary napkin 1C and on the skin noncontacting side of the front end portion in the front region (F). More specifically, the cover member 15C and the sanitary napkin main body 5C are joined with each other on both side portions of the back sheet portion 3 and at the front end of the front region (F).

As shown in FIGS. 14 to 16D, the cover member 15C, in a projected state, may also be joined with the back sheet portion 3 in the both side portions of the sanitary napkin 1C and in the front end portion of the front region (F).

The length of the cover member 15C in the longitudinal direction (LD) can be exemplified, for example, to be preferably in the range of 10 to 100% of the length of the sanitary napkin main body 5C in the longitudinal direction (LD), and more preferably in the range of 50 to 90% thereof. In a case where the length of the cover member 15C in the longitudinal direction (LD) is less than 10% thereof, for example, the degree of freedom between the sanitary napkin main body 5C and the belt-shaped member 10C is too large, and there is a risk of displacement during wearing as a result. Alternatively, in a case where the length of the cover member 15C in the longitudinal direction (LD) is greater than 100%, for example, there is an obstacle when expanding and engaging the belt-shaped member 10C with the underwear 50 as a result.

The length of the cover member 15C in the width direction (WD) can be exemplified, for example, to be preferably in the range of 30 to 150% of the length of the sanitary napkin main body 5C in the width direction (WD), and more preferably in the range of 50 to 110% thereof. In a case where the length in the width direction (WD) of the cover member 15C is less than 30% thereof, for example, the sanitary napkin main body 5C cannot sufficiently adhere to the wearer's body as a result. Alternatively, in a case where the length in the width direction (WD) of the cover member 15C is greater than 150% thereof, for example, the area to be in contact with the thighs is excessive, and there is a risk of skin irritation due to frictional contact or the like as a result.

In addition, the length of the cover member 15C in the width direction (WD) can be exemplified, for example, to be preferably in the range of 100 to 200% of the length of the belt-shaped member 10C in the width direction (WD), and more preferably in the range of 105 to 150% thereof. In a case where the length in the width direction (WD) of the cover member 15C is less than 100% thereof, for example, the belt-shaped member 10C cannot be expanded smoothly as a result. Alternatively, in a case where the length in the width direction (WD) of the cover member 15C is greater than 200%, for example, since the degree of freedom of the belt-shaped member 10C in the width direction (WD) is too large, there is likelihood for misalignment between the central axis of the sanitary napkin main body 5C and the central axis of the belt-shaped member 10C as a result.

The cover member 15C may be constituted of either a different material from the construction materials of the sanitary napkin main body 5C, or may use identical materials to any one of the construction materials of the sanitary napkin main body 5C. In this case, a common construction material may be elongated so as to continuously form the cover member 15C. For example, an extension portion of the top sheet portion 2 or the back sheet portion 3 may be used therefor. In the case where an extension portion of the top sheet portion 2 or back sheet portion 3 is used, the respective sheets disposed continuously may be overlapped and connected to each other on the skin noncontacting side. More specifically, 50% or more of the length of the sanitary napkin main body 5C in the width direction (WD) may be continuous and the respective elongated sheets may be folded back for lamination and connection, at the substantially central portion in the width direction (WD) on the skin noncontacting side of the sanitary napkin main body 5C (see FIG. 16D).

As a fifth embodiment, the cover member 15D may be arranged in the rear region (R) of the sanitary napkin main body 5D as shown in FIG. 17. Alternatively, as shown in FIG. 18A, both side portions of the cover member 15D can be folded inside the sanitary napkin main body 5D and joined with the back sheet portion 3. This arrangement allows for a large frontage between the back sheet portion 3 and the cover member 15D, thereby allowing an easy expansion of the belt-shaped member 10D.

Alternatively, as shown in FIG. 18B, an elastic member 16 may be arranged at each of the folded portions of the cover member 15D on both side portions in the width direction (WD) of the sanitary napkin main body 5D. By such an arrangement, for example, even if the sanitary napkin main body 5D or the belt-shaped member 10D has a tendency to twist, the elasticity of the elastic member 16 produces a force to restore the sanitary napkin main body 5D or the belt-shaped member 10D from the twist, thereby preventing the twist thereof.

As a sixth embodiment, as shown in FIGS. 19A and 19B, the cover member 15E may be disposed so as to cover the engaging portion 9r of the belt-shaped member 10E. In this case, when the belt-shaped member 10E is in a non-expanded state, the grip portion 6E of the belt-shaped member 10E is projected from the outer edge in the rear region (R) of a sanitary napkin main body 5E in the longitudinal direction (LD), and the engaging portion 9r is covered with a cover member 15E. Thus, by covering the engaging portion 9r with the cover member 15E, for example, the engaging portion 9r can be prevented from sticking to any unintentional location before expanding the belt-shaped member 10E. In addition, by projecting the grip portion 6E, for example, since the wearer is able to easily pinch the grip portion 6E, operability is improved.

Furthermore, a silicon resin or the like may be coated on the surface of the cover member 15E. This is preferable because the coating of the silicon resin or the like prevents the engaging portion 9r from sticking to the cover member 15E. Alternatively, the surface of the engaging portion 9r may be covered with a release paper or the like.

A plurality of cover members 15E may be provided, and are preferably arranged at least in the vicinity of the rear region (R) region of the sanitary napkin main body 5E. By arranging in the vicinity of the rear region (R) of the sanitary napkin main body 5E, slippage of the belt-shaped member 10E from the sanitary napkin main body 5E during wearing can be prevented as a result.

As a seventh embodiment, as shown in FIGS. 20 to 21B, engaging portions 91R and 91L to be engaged with the underwear 50 may be arranged in both side, respectively, of a substantially central portion in the longitudinal direction (LD) of a cover member 15F. By arranging engaging portions 91R and 91L in both side portions, the underwear 50 can also be lifted to the wearer's body by the tension of the belt-shaped member 10F and, for example, dislocation between the sanitary napkin 1F and the underwear 50 can be prevented.

A plurality of, for example, two, engaging portions 91R and 91L, as shown in FIG. 20, may be arranged in both sides of a substantially central portion of the cover member 15F in the longitudinal direction (LD); however, the engaging portions may be arranged throughout the width direction (WD) of the substantially central portion in the longitudinal direction (LD) of the cover member 15F. Alternatively, arrangement may be from the substantially central portion to the rear region (R) of the cover member 15F. Furthermore, arrangement may be throughout the entirety of the cover member 15F.

Alternatively, as shown in FIG. 21B, an elastic member 16 may be arranged at each of the folded portions of the cover member 15F on both side portions in the width direction (WD) of the sanitary napkin main body 5F. In this arrangement, for example, even if the sanitary napkin main body 5F or the belt-shaped member 10F has a tendency to twist, the elasticity of the elastic member 16 produces a force to restore the sanitary napkin main body 5F or the belt-shaped member 10F from the twist, thereby preventing the twist thereof.

2-4. Eighth Preferred Embodiment

A sanitary napkin 1G of the eighth embodiment of the present invention is described with reference to FIGS. 22A and 22B. As shown in FIGS. 22A and 22B, the eighth embodiment of the present invention is different from the first embodiment in the location of the belt-shaped member 10G.

More specifically, in the sanitary napkin 1G of the eighth embodiment, the belt-shaped member 10 is provided between the absorbent core portion 4 and the back sheet portion 3. In this case, the top sheet portion 2 and the back sheet portion 3 are joined with each other in both side portions of the sanitary napkin 1G and in the front end portion of the front region (F), as shown in FIG. 22B. The belt-shaped member 10G projects from an opening, which is a non-joined portion in the rear region (R) of the sanitary napkin 1G.

In the eighth embodiment, the belt-shaped member 10G may be arranged between the top sheet portion 2 and the absorbent core portion 4. Alternatively, in a case where an absorbent core portion (not shown) is constituted of a plurality of layers, the belt-shaped member 10G may be interposed between the layers thereof. The belt-shaped member 10G is preferably hydrophilic and liquid permeable. This can effectively facilitate mobility of excrement such as menstrual blood from the top sheet portion 2 to the absorbent core portion 4.

2-5. Ninth Preferred Embodiment

A sanitary napkin 1H of the ninth embodiment of the present invention is described with reference to FIG. 23. As shown in FIG. 23, the sanitary napkin 1H of the ninth embodiment of the present invention is different from the first embodiment in that the engaging portion 9r to be engaged with the underwear 50 is not provided in a belt-shaped member 10H in the rear region (R). The sanitary napkin 1H of the ninth embodiment does not necessarily have the engaging portion 9r to be engaged with the underwear 50 in the rear region (R).

Mode of usage in this case includes the following. For example, after pulling down the underwear 50 to the wearer's knees, engaging portions 9f, 91R, and 91L are fixed to the underwear 50 in the front region (F) and at both side portions of a sanitary napkin main body 5H, respectively, and the underwear 50 is then put on. Subsequently, from the back of the wearer's body, a hand is put between the underwear 50 and the wearer's body, the grip portion 6H is pinched, and the belt-shaped member 10H is pulled along the curvature of the wearer's body toward the rear region (R) and inserted in the groove in the vicinity of the excretory part, more specifically, the groove in the vicinity of the buttocks.

2-6. Tenth and Eleventh Preferred Embodiments

Sanitary napkins 1I and 1J of the tenth and eleventh embodiments of the present invention are described with reference to FIGS. 24 to 26C. As shown in FIGS. 24 to 26C, the sanitary napkins 1I and 1J of the tenth and the eleventh embodiments are different from the first embodiment in having a guide element. More specifically, in the sanitary napkin 1I and 1J of the tenth and the eleventh embodiments, the grip portions 6Ir, 6If and 6J may be provided with the guide element 70 that indicates the directions of expansion of the belt-shaped members 10I and 10J.

As the guide element 70, for example, an indication sign sheet with arrows, symbols, illustrations, characters, colors, color gradation or the like, and a guide element attained by touch sense of embossing or the like can be exemplified. Alternatively, for example, the guide element 70 may be provided by a patterning process of a hot melt adhesive on the skin-contacting side or on the skin noncontacting side of the grip portions 6Ir, 6If, and 6J. In addition, with a composite as shown in FIG. 5A, composed of the base material sheets 11 and 13 and the elastic member 12, in a case where the guide element 70 is formed by a colored patterning process of a hot melt adhesive, the base material sheets 11 and 13 in the grip portions 6Ir, 6If, and 6J can be thereby joined with each other. Alternatively, for example, an indication sign sheet with a guide sign or the like printed thereon may be interposed between the base material sheets 11 and 13. In addition, direct printing may be on the base material sheets 11 and 13.

In the tenth embodiment, as shown in FIG. 24, since the grip portions 6If and 6Ir project from the outer edge portion in the front region (F) and the rear region (R) of the sanitary napkin main body 5I in the longitudinal direction (LD), and the skin-contacting side of the grip portions 6If and 6Ir is exposed, for example, the grip portions 6If and 6Ir can be easily found by the wearer, and operability is improved. Alternatively, for example, the grip portions 6If and 6Ir may have a different color from the surroundings in the belt-shaped member 10I. In addition, for example, a symbol, an illustration, or a character may be used. Alternatively, for example, the grip portions 6If and 6Ir may be in the shape of a triangle, a circle, an ellipse, or corrugation.

In the eleventh embodiment, since the grip portion 6J projects from the outer edge portion in the rear region (R) of the sanitary napkin main body 5J in the longitudinal direction (LD), and the skin-contacting side of the grip portion 6J is exposed, for example, the grip portion 6J can be found easily by the wearer, and operability is improved. Alternatively, for example, the grip portion 6J may have a different color from the surroundings in the belt-shaped member 10J. In addition, for example, a symbol, an illustration, or a character may be used. Alternatively, the grip portion 6J may be in the shape of a triangle, a circle, an ellipse, or corrugation.

In addition, as shown in FIG. 25, the grip portions 6If and 6Ir may have a guide element 70' on the grip portions 6If and 6Ir, for suggesting the position of the engaging portions 9f and 9r to be engaged with the underwear 50 as another embodiment. For example, in FIG. 25, the sanitary napkin 1I' is exemplified as arranging a colored sheet on the surface where the engaging material is provided at the engaging portions 9f and 9r to be engaged with the underwear 50. As the guide element 70' for suggesting the position of the engaging portions 9f and 9r, a colored sheet can be exemplified. In addition, embossing, printing, colored hot melt adhesive, and the like can be exemplified as the guide element 70'. Furthermore, the belt-shaped member 10I' may be constituted of a sheet of high transparency, to make the engaging portions 9f and 9r, disposed on the back sheet portion 3, visible.

2-7. Twelfth to Fourteenth Preferred Embodiments

Sanitary napkins 1K, 1L and 1M of the twelfth to fourteenth embodiments of the present invention are described with reference to FIGS. 27A to 29. As shown in FIGS. 27A to 29, the sanitary napkins 1K, 1L and 1M of the twelfth to the fourteenth embodiments of the present invention are different from the first embodiment in having a guide element. More specifically, the sanitary napkins 1K, 1L and 1M may have a guide element for suggesting the liquid permeable region 21 of the sanitary napkin 1.

In the twelfth embodiment, as shown in FIG. 27A, for example, wings W1 and W2 may be disposed on both side portions of the sanitary napkin 1K, in order to imply that the liquid permeable region 21 is present at the substantially central portion in the width direction (WD) of the wings W1 and W2.

In the thirteenth embodiment, as shown in FIG. 28, guide elements 71 having a different color may be disposed, for example, at a predetermined position on both side portions of the sanitary napkin 1L, in order to imply that the liquid permeable region 21 is present at the substantially central portion in the width direction (WD) of the guide elements 71.

As an implication of the liquid permeable region 21, for example, the position corresponding to the wearer's excretory part, as well as the positions in front and the rear thereof may be specified.

In the fourteenth preferred embodiment, as shown in FIG. 29, for example, a guide element 72 for implying the rear region (R) may be provided at a predetermined position of the grip portion 6M of a belt-shaped member 10M. The guide element 72 can be exemplified as being forming by embossing, colored hot melt, printing, or the like. Alternatively, the implying matter may be made different in color from the surroundings. In addition, the implying matter may be made by color gradation, a symbol, an illustration, a character, or a graphic symbol.

As an additional embodiment to the aforementioned embodiments, the belt-shaped member may be used as an auxiliary pad by applying it to the skin-contact surface of another sanitary napkin main body. In this case, the present invention is preferably shorter in length in the width direction (WD) and in the longitudinal direction (LD) than the sanitary napkin main body to be used therewith. Furthermore, the auxiliary pad of the present invention may be entirely constituted of a liquid permeable material, or a liquid impermeable material partially having liquid-permeable pores, in order to facilitate the transfer of menstrual blood from the auxiliary pad to another sanitary napkin. The menstrual blood leaking out of the auxiliary pad can thus be absorbed in another sanitary napkin. In addition, the belt-shaped member of the present invention is projected from the sanitary napkin main body and, in a case where an engaging member is provided, can be used as a belt-shaped tape for disposal of the sanitary napkin.

3. Components

The components of the sanitary napkin are described hereinafter.

3-1. Sanitary Napkin Main Body 3-1-1. Top Sheet Portion

The top sheet portion 2 is disposed on the wearer's body side, and is also brought into contact with the excretory part during wearing. The top sheet portion 2 may be entirely liquid permeable or partially liquid permeable. In addition, the top sheet portion 2 may be composed of either a single sheet-like member or a plurality of sheet-like members bonded together.

A woven fabric, a non-woven fabric, or a sheet material having liquid permeability such as a porous plastic sheet can be used for the top sheet portion 2. For example, as the woven fabric or the non-woven fabric, natural fibers and chemical fibers can be exemplified. More specifically, celluloses such as pulverized pulp and cotton can be exemplified as the natural fiber. In addition, regenerated celluloses such as rayon and fibril rayon; semi-synthetic celluloses such as acetate and triacetate; thermoplastic hydrophobic chemical fiber; and hydrophilized thermoplastic hydrophobic chemical fiber can be exemplified as the chemical fiber. Single fibers made of polyethylene (PE); polypropylene (PP); polyethylene terephthalate (PET); fibers obtained by graft polymerizing polyethylene (PE) with polypropylene (PP); composite fibers having core/sheath structure; and the like, for example, can be exemplified as the thermoplastic hydrophobic chemical fiber.

Furthermore, in a case where a non-woven fabric is used, dry or wet web forming such as a carding process, spun bond process, melt blown process, and air-laid process can be used. In addition, the dry and wet web forming methods may be combined. A method of bonding includes thermal bonding, needle punch, chemical bonding, and the like, without limiting thereto. Alternatively, a spun lace formed in a sheet-like shape by a spun lace process may be used.

A perforated sheet of thermoplastic resin such as polyethylene (PE), polypropylene (PP) or polyethylene terephthalate (PET); and a perforated sheet of a porous foamed material, for example, can be exemplified as the perforated plastic sheet.

Furthermore, it is preferred to use a porous plastic clouded by adding in the range of 0.5 to 10% of filler such as titanium oxide and calcium carbonate. Alternatively, a film obtained by providing pores on a thermoplastic resin film by perforation, heat embossing finish, or cutting may be used. The porous film may be combined with the non-woven fabric, and a composite sheet thus obtained may be used.

3-1-2. Absorbent Core Portion

The absorbent core portion 4 is required to have functions of absorbing and retaining excrement such as menstrual blood, and is preferably a bulky material that causes little chemical irritation and hardly loses its shape. For example, celluloses such as pulverized pulp and cotton, regenerated celluloses such as rayon and fibril rayon, semi-synthetic celluloses such as acetate and triacetate, particulate polymer, fibrous polymer, thermoplastic hydrophobic chemical fiber, thermoplastic hydrophobic chemical fiber subjected to hydrophilization, and air-laid pulp subjected to a chemical bond process can be used singly or in combination.

Furthermore, although no special limitation is imposed on the method of forming these materials in the absorbent core portion 4, an air-laid process, a melt blown process, a spun lace process, or a paper making process can be used, for example, and a sheet thus formed can be used.

Cellulose foam or continuous foam of synthetic resin can also be used as the absorbent core portion 4. Furthermore, a foam material or a sheet-shaped material may be pulverized and then formed in an absorbent core.

Among these, a preferred sheet-shaped absorbent core has a fiber weight of 100 to 2000 $g/m^2$, and a length in bulk of 1 to 50 mm, which can be obtained by blending 80 to 100% of pulp with no greater than 20% of particulate polymer, then covering with a tissue, followed by an embossing finish. The embossing finish is for preventing the absorbent core from losing its shape, and the embossed area is preferably in the range of 10 to 100%, and more preferably 30 to 80%.

Furthermore, an absorption sheet and a polymer sheet, for example, can be given as other examples of the material for the absorbent core portion 4. The thickness of the absorption sheet and polymer sheet are preferred to be 0.3 to 5.0 mm. An absorption sheet and a polymer sheet used for absorbent articles such as sanitary napkins may be used.

Examples of the absorption sheet include: an absorption paper; a non-woven fabric; and a pulp sheet obtained by processing fiber with a binder. Examples of the polymer sheet include: a pulverized pulp; and a sheet obtained by blending a particulate polymer in fiber and processing the mixture into a sheet. Furthermore, in the sheet thus obtained, the particulate polymer may be dispersed in the shape of a layer or in a three dimensional form.

The material used for the absorption sheet and the fiber used in the polymer sheet preferably includes: cellulose fibers such as wood pulp; regenerated celluloses such as rayon and cupra; hydrophilic synthetic fibers such as a polyvinyl alcohol fiber; a polyacrylonitrile fiber; and fibers such as polyethylene, polypropylene, polyethylene terephthalate, a polyethylene/polypropylene composite fiber, and a polyethylene/polyethylene terephthalate composite fiber, of which a surface is hydrophilized by a surface active agent. The cellulose fiber is more preferable in consideration of hydrophilic properties.

A polymer that can absorb and retain liquid at least 20 times as heavy as its own weight and can be gelatinized is preferably used for the polymer sheet. Examples of such a polymer include: starch, cross-linked carboxymethyl cellulose, polyacrylic acid and a salt thereof, polyacrylate graft copolymer and the like.

3-1-3. Back Sheet Portion

For the back sheet portion 3, a thermoplastic film composed mainly of polyethylene (PE) or polypropylene (PP), a permeable resin film, a sheet obtained by joining a permeable resin film with a non-woven fabric such as spun bond or spun lace, a multilayer of SMS (spun bond/melt blown/spun bond), or the like can be used. Preferable, for example, is a film composed mainly of low-density polyethylene (LDPE) resin having a fiber weight in the range of 15 to 30 $g/m^2$ for its flexibility and comfort during wearing.

In addition, in a case where a liquid impermeable sheet is used in the belt-shaped member, the same liquid permeable sheet as the top sheet portion 2 can be used as the back sheet portion 3.

3-1-4. Joining Portion

The top sheet portion 2 and the absorbent core portion 4 are adhesively joined to each other with a hot melt adhesive. In addition, the top sheet portion 2 and the back sheet portion 3 are adhesively joined with each other at a joining portion formed with a hot melt adhesive and by hot pressing, or the like. In the entirety, surfaces of the sheets are joined with each other with the hot melt adhesive, and edge portions of each sheet are joined by the joining portion formed by the hot pressing process. Furthermore, the joining method is not limited to the hot melt adhesion and, for example, a heat embossing finish, ultrasonic waves, etc. may also be used singly or in combination.

The coating patterns for the hot melt adhesion include, for example, spiral coating, controlled seam coating, coater coating, curtain coater coating, summit-gun coating and the like. The weight of the adhesive in the hot melt adhesion is preferably 1 to 30 $g/m^2$, and more preferably 3 to 10 $g/m^2$. In addition, in a case where adhesive is coated in a linear pattern, the diameter thereof is preferably from 30 to 300 μm.

3-2. Belt-Shaped Member 3-2-1. Overall Configuration

For example, a fibrous sheet using thermoplastic elastomer resin may be used for the belt-shaped member 10. More specifically, a non-woven fabric obtained by blending urethane fiber and synthetic fiber; a non-woven fabric including a layer obtained by forming elastomer resin by melt blowing; and a film sheet can be exemplified.

In addition, as shown in FIG. 5A, a composite composed of the base material sheets 11 and 13 and the elastic member 12 can be used as the belt-shaped member 10 as another embodiment. A belt-shaped member 10' composed of the composite can be obtained by, for example: interposing the elastic member 12 virtually without tension, between the base material sheets 11 and 13 of which fiber orientation is random or subjectively in the width direction (WD) of the belt-shaped member; joining the elastic member 12 with the base material sheets 11 and 13; and fixing the composite to the sanitary napkin main body 5. Since the fiber orientation of the base material sheets 11 and 13 is subjectively in the width direction (WD) of the belt-shaped member, the fiber form thereof can be easily deformed when the belt-shaped member 10' is expanded in the longitudinal direction (LD), and thus the belt-shaped member can be neck-in with a light load.

3-2-2. Base Material Sheet

For the base material sheets 11 and 13, by creating a difference in peripheral speed at the time of web forming and the like, the fiber orientation thereof may be made random, or by, for example, rotating non-woven fabrics of parallel orientations 90 degrees, may be arranged so as to be orthogonal to the elastic member 12. Regarding a case in which the back sheet portion 3 is a liquid impermeable sheet, for example, the base material sheets 11 and 13 of the belt-shaped member 10 can be the liquid permeable sheet as exemplified as the top sheet portion 2. The base material sheets 11 and 13 are exemplified by a thin non-woven fabric such as a spun bond non-woven fabric, point bond non-woven fabric, and spun lace non-woven fabric, for example. This is because a thinner non-woven fabric provides enhanced smoothness of the belt-shaped member in the stretched state. In addition, in a case where a concave and convex shape is to be applied by the corrugated embossing finish described in the first embodiment, for example, a spun bond non-woven fabric composed of a continuous fiber is preferably used, in order to prevent the non-woven fabric from being broken during a corrugated embossing finish process.

In a case where the back sheet portion 3 is a liquid permeable sheet, each of the base material sheets 11 and 13 of the belt-shaped member 10 can be the liquid impermeable sheet as exemplified above as the back sheet portion 3. The liquid impermeable sheet may be disposed only on the skin-contacting side with respect to the elastic member, or disposed on both the skin-contacting and the skin noncontacting sides.

3-2-3. Elastic Member

Examples of the elastic member 12 include, for example, an elastic yarn of natural rubber or polyurethane. More specifically, foams of an elastomer component or polyethylene foam can be used singly; alternatively, a string, a belt or a sheet obtained by processing a mixture including thereof can be used.

Examples of the elastomer component include: a thermoplastic elastomer of polyester, urethane, olefin, styrene, or polyamide; low density polyethylene using metallocene catalyst; and ethylene-α-olefin copolymer. These can be used singly or in combination.

As the polyester elastomer, for example, one having a hard segment of aromatic polyester and a soft segment of non-crystal polyether or aliphatic polyester can be exemplified.

As the urethane elastomer, for example, a polyurethane composed of polyester, low molecular weight glycol, and methylene bisphenyl isocyanate, in which polylactone ester polyol is addition polymerized with polyisocyanate in the presence of short chain polyol can be provided.

As the olefin elastomer, for example, ethylene-α-olefin random copolymer and one copolymerized with diene as a third composition can be exemplified.

As the styrene elastomer, block copolymers such as SEBS, SIS, SEPS, and SBS can be exemplified.

As the polyamide elastomer, for example, one of which a hard segment is nylon and a soft segment is polyester or polyol can be exemplified.

In addition, in order to stabilize the formation of the elastic member, the constitutive polymer of the elastomer component may contain, for example, high density polyethylene, low density polyethylene, linear low density polyethylene or the like. Furthermore, it may combine a blocking inhibitor, ultraviolet absorbing agent, thickening and branching agent, flatting agent, coloring agent, and other conditioning agents. Among these, the polyurethane elastic yarn is preferred for its effects related to resistibility against heat and strain.

3-2-4. Joining Material

As the joining material in joining the base material sheets 11 and 13 with the elastic member 12, or joining the base material sheet 11 with the base material sheet 13, for example, a heat embossing finish, ultrasonic waves, a hot melt adhesive, etc. can be used singly or in a combination thereof. For example, a hot melt adhesive is applied to the base material sheet 11 by a coating method such as spiral coating, coater coating, curtain coater coating, or summit gun coating, the elastic material 12 is laid thereon, and then the base material sheet 13 is laid thereon and joined together. In order to prevent the elastic member 12 from separating from the base material sheets 11 and 13, the elastic member 12 may be coated in advance by a coating method such as slit coating or control seam coating.

Examples of the hot melt adhesive include, for example: pressure sensitive adhesives and thermo-sensitive adhesives, each composed mainly of rubbers such as SEBS, SBS, and SIS or olefins such as linear low-density polyethylene; and water-sensitive adhesives of polyvinyl alcohol, carboxyl methyl cellulose, or gelatin, each being composed of water soluble high polymer, or of polyvinyl acetate or polyacrylic acid sodium, each being composed of a water swelling high polymer. It is preferable to use, for example, a heat sensitive adhesive that, even if the aforementioned adhesive effuses, has no tackiness at that point in time. As a more specific example, such an adhesive is exemplified by a melt-mixture in the range of 5 to 25% of SEBS, 40 to 60% of alicyclic saturated hydrocarbon, 1 to 10% of aromatic denaturated terpene, and 15 to 35% of additive.

3-3. Engaging Material

Examples of the engaging material for the engaging portion 9 for engaging the sanitary napkin main body to the underwear 50 include, for example, a hot melt adhesive. As a hot melt adhesive, for example, having inherent tackiness is preferred, and a pressure-sensitive adhesive can be exemplified. The main component of the adhesive is the same as in the abovementioned joining material; more specifically, examples thereof include a melt-mixture of 15 to 25% of SEBS, 15 to 35% of plasticizer, and 40 to 70% of an adhesive-imparting agent. In addition, an oxidation inhibitor and a fluorescence inhibitor may be added in the range of 0.1 to 1.0%. The basis weight is from 10 to 200 gsm, and coated uniformly or in a streak pattern or in dots, by coater coating or bead coating. Alternatively, an acrylic adhesive may be used. Furthermore, the engagement may be attained by using a plurality of hook parts that stand on the surface of each tape-shaped portion.

More specifically, the tape-shaped portion can be formed by extrusion molding of a thermoplastic synthetic resin such as polypropylene, followed by cutting and removal of a rib structure part integrally formed with the tape-shaped portion. In addition, a hook portion may be formed by cutting from a side a monofilament loop composed of thermoplastic synthetic resin that is provided on the surface of the tape-shaped portion. Furthermore, the end face of the hook part may be rounded in order to eliminate the risk of damaging the skin. In order to eliminate the risk of damaging the skin, the hook part may have a rounded shape. More specifically, the top of the hook can be rounded with the shape of a die. Furthermore, no special limitation is imposed on the cross-sectional shape of the hook part, and it may be tapered or of T-shape.

On the other hand, examples of engaging portion 9 to be fixed to the wearer's body and not to the underwear 50, in a case where the engaging portion 9 is provided on the skin-contacting side of the belt-shaped member 10, include a water-soluble polymer, cross-linking agent, plasticizer, gel adhesive composed of water, and the like. More specifically, gelatin, polyacrylic acid sodium, polyvinyl alcohol, and carboxyl methyl cellulose can be exemplified as the water-soluble polymer. Water-soluble metallic salts such as calcium chloride and magnesium sulfate. Example of the plasticizer includes glycerine, wax, and paraffin can be exemplified as the cross-linking agent.

Furthermore, with respect to the pressure-sensitive adhesive and the engaging portion 9, the part having tackiness is preferably covered with a sheet obtained by coating a silicon resin on thin paper, in other words generally available release paper, or a sheet obtained by coating silicon resin on a film. This can protect the adhesive portion against dirt or release during storage.

The invention claimed is:

1. An absorbent article having a substantially elongated shape, comprising:
    an absorbent article main body at least including:
        a top sheet portion that is at least partially liquid permeable and disposed at a first side of the absorbent article main body in a thickness direction of the absorbent article,
        a back sheet portion that is liquid impermeable and disposed at a second side of the absorbent article main body opposite to the first side, and
        a liquid retentive absorbent core portion that is disposed between the top sheet portion and the back sheet portion in the thickness direction of the absorbent article; and
    a single belt-shaped member disposed on the second side of the absorbent article main body, along a longitudinal direction of the absorbent article main body,
    a pair of joining portions located at the back sheet portion of the absorbent article main body and spaced a predetermined distance apart from each other across a center in a width direction perpendicular to the longitudinal direction of the absorbent article main body at transversely opposite side portions of the absorbent article main body; and
    a connecting member directly connecting the joining portions to each other, arranged on the absorbent article main body on the second side, and adapted to face away from a wearer when the absorbent article is worn on the wearer, wherein the connecting member is elongated in the width direction of the absorbent article main body,
    wherein
    the belt-shaped member, in the longitudinal direction, has a first end connected to each of the joining portions via the connecting member, and
    in a state where the belt-shaped member is pulled in the longitudinal direction, the absorbent article body is adapted to form a convex portion and a distance between the pair of joining portions decreases, wherein the connecting member has two end sections opposite to each other in the width direction and directly attached to the joining portions, respectively, and a middle section between said two end sections in the width direction, wherein said middle section is free of direct attachment to the absorbent article main body, and said middle section is directly attached to the belt-shaped member.

2. The absorbent article according to claim 1,
    wherein the belt-shaped member further comprises a grip portion arranged in a second end of the belt-shaped member opposite to the first end in the longitudinal direction and including at least a part that projects beyond an outer peripheral portion of the absorbent article main body in the longitudinal direction.

3. The absorbent article according to claim 1, further comprising a cover member on the second side of the absorbent article main body, and encapsulating at least a part of a length of the belt-shaped member in the longitudinal direction and an entirety of a width of the belt-shaped member in the width direction.

4. The absorbent article according to claim 2,
    wherein the grip portion has a guiding element for indicating an expansion direction of the belt-shaped member.

5. The absorbent article according to claim 1,
    wherein a width of the belt-shaped member in the width direction is at least 30% of a width of the absorbent article main body in the width direction.

6. The absorbent article according to claim 1, wherein
    the joining portions are adapted to be brought together by deforming the deformable region to become narrower in the width direction, and
    the absorbent article main body is adapted to be deformed to be convex to the first side.

7. The absorbent article according to claim 6,
    wherein a projecting height of the convex deformation of the absorbent article main body is adjustable, by adjusting a position of the belt-shaped member with respect to the absorbent article main body in the longitudinal direction, thereby adjusting a distance between the joining portions.

\* \* \* \* \*